United States Patent
Reddy et al.

(10) Patent No.: US 10,034,891 B2
(45) Date of Patent: Jul. 31, 2018

(54) INHIBITORS OF DIACYLGLYCEROL O-ACYLTRANSFERASE 1 (DGAT-1) AND USES THEREOF

(71) Applicant: METABASIS THERAPEUTICS, INC., La Jolla, CA (US)

(72) Inventors: K. Raja Reddy, San Diego, CA (US); Jeff Stebbins, San Diego, CA (US); Serge H. Boyer, San Diego, CA (US); Mark D. Erion, Del Mar, CA (US); Scott J. Hecker, Del Mar, CA (US); Nicholas Brian Raffaele, San Diego, CA (US); Brett C. Bookser, San Diego, CA (US); Venkat Reddy Mali, Cupertino, CA (US)

(73) Assignee: Metabasis Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/151,740

(22) Filed: May 11, 2016

(65) Prior Publication Data
US 2016/0263132 A1     Sep. 15, 2016

Related U.S. Application Data

(60) Continuation of application No. 14/628,373, filed on Feb. 23, 2015, now Pat. No. 9,340,566, which is a
(Continued)

(51) Int. Cl.
| | | |
|---|---|---|
| *A01N 43/82* | (2006.01) |
| *A61K 31/41* | (2006.01) |
| *A61K 31/675* | (2006.01) |
| *A61K 31/542* | (2006.01) |
| *A61K 31/52* | (2006.01) |
| *A61K 31/662* | (2006.01) |
| *A61K 31/665* | (2006.01) |
| *A61K 45/06* | (2006.01) |
| *C07D 473/16* | (2006.01) |
| *C07D 473/34* | (2006.01) |
| *C07D 473/40* | (2006.01) |
| *C07F 9/30* | (2006.01) |

(Continued)

(52) U.S. Cl.
CPC ......... *A61K 31/675* (2013.01); *A61K 31/52* (2013.01); *A61K 31/542* (2013.01); *A61K 31/662* (2013.01); *A61K 31/665* (2013.01); *A61K 31/683* (2013.01); *A61K 31/688* (2013.01); *A61K 45/06* (2013.01); *C07D 473/16* (2013.01); *C07D 473/34* (2013.01); *C07D 473/40* (2013.01); *C07F 9/303* (2013.01); *C07F 9/3229* (2013.01); *C07F 9/40* (2013.01); *C07F 9/48* (2013.01); *C07F 9/6552* (2013.01); *C07F 9/6561* (2013.01); *C07F 9/65312* (2013.01); *C07F 9/65616* (2013.01); *C07F 9/65742* (2013.01)

(58) Field of Classification Search
None
See application file for complete search history.

(56) References Cited

U.S. PATENT DOCUMENTS

| | | |
|---|---|---|
| 6,110,903 A | 8/2000 | Kasibhatla et al. |
| 6,399,782 B1 | 6/2002 | Kasibhatla et al. |

(Continued)

FOREIGN PATENT DOCUMENTS

| | | |
|---|---|---|
| WO | WO 2004/047755 | 6/2004 |
| WO | WO 2005/044250 | 5/2005 |

(Continued)

OTHER PUBLICATIONS

Birch, A. M. et al. "Discovery of a Potent, Selective, and Orally Efficacious Pyrimidinooxazinyl Bicyclooctaneacetic Acid Diacylglycerol Acyltransferase-1 Inhibitor" *Journal of Medicinal Chemistry*, 2009, pp. 1558-1568, vol. 52, No. 6.
Freeman, S. et al, "Prodrug Design for Phosphates and Phosphonates" *Progress in Medicinal Chemistry*, 1997, pp. 111-147, vol. 34.
He, G.-X. et al. "Chapter 3.6. Prodrugs of Phosphonates, Phosphinates, and Phosphates" *Prodrugs Challenges and Rewards Part 1* (Book Series: Biotechnology: Pharmaceutical Aspects), Jan. 1, 2007, pp. 923-964.
Written Opinion in International Application No. PCT/US2010/027889, dated Sep. 21, 2010, pp. 1-13.
Guerre-Millo, M. et al. "Peroxisome Proliferator-activated Receptor a Activators Improve Insulin Sensitivity and Reduce Adiposity" *The Journal of Biological Chemistry*, Jun. 2, 2000, pp. 16638-16642, vol. 275, No. 22.
Bonora, E. et al. "Estimates of in Vivo Insulin Action in Man: Comparison of Insulin Tolerance Tests with Euglycemic and Hyperglycemic Glucose Clamp Studies" *Journal of Clinical Endocrinology and Metabolism*, 1989, p. 374-378, vol. 68, No. 2.
Bergman, R. N. et al. "Assessment of Insulin Sensitivity in Vivo" *Endocrine Reviews*, 1985, pp. 45-86, vol. 6, No. 1.
Kalek, M. et al. "Microwave-Assisted Palladium-Catalyzed Cross-Coupling of Aryl and Vinyl Halides with H-Phosphonate Diesters" *Organic Letters*, 2008, pp. 4637-4640, vol. 10, No. 20.

(Continued)

*Primary Examiner* — Jeffrey H Murray
(74) *Attorney, Agent, or Firm* — Knobbe Martens Olson & Bear LLP

(57) ABSTRACT

The invention pertains to the use of compounds represented by the formula, $Q\text{-}G^1\text{-}G^2\text{-}G^3\text{-}G^4\text{-}Z$, where Q is

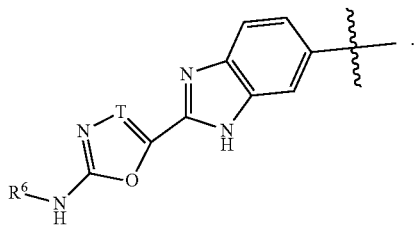

The compounds can be used as diacylglycerol O-acyltransferase 1 (DGAT-1) inhibitors to treat hyperlipidiemias and various diseases and disorders associated therewith. Other conditions also can be ameliorated or avoided, such as high postprandial triglycerides or diet-related hypertriglyceridemia, cardiovascular risk associated with excessive triglycerides, and insulin resistance/glucose intolerance in overweight patients, those with diabetes or other glucose metabolic disorders such as Syndrome X and/or polycystic ovary disease.

4 Claims, No Drawings

Related U.S. Application Data division of application No. 13/458,452, filed on Apr. 27, 2012, now Pat. No. 8,962,618, which is a continuation of application No. 13/256,952, filed as application No. PCT/US2010/027889 on Mar. 19, 2010, now abandoned.

(60) Provisional application No. 61/162,170, filed on Mar. 20, 2009.

(51) Int. Cl.

| | | |
|---|---|---|
| *C07F 9/32* | (2006.01) | |
| *C07F 9/653* | (2006.01) | |
| *C07F 9/6561* | (2006.01) | |
| *C07F 9/6574* | (2006.01) | |
| *C07F 9/48* | (2006.01) | |
| *C07F 9/655* | (2006.01) | |
| *A61K 31/683* | (2006.01) | |
| *A61K 31/688* | (2006.01) | |
| *C07F 9/40* | (2006.01) | |

(56) References Cited

U.S. PATENT DOCUMENTS

| | | |
|---|---|---|
| 6,489,476 B1 | 12/2002 | Dang et al. |
| 6,919,322 B2 | 7/2005 | Bookser et al. |
| 6,965,033 B2 | 11/2005 | Jiang et al. |
| 6,967,193 B1 | 11/2005 | Dang et al. |
| 8,962,618 B2 * | 2/2015 | Reddy ............ A61K 31/52 514/224.2 |

FOREIGN PATENT DOCUMENTS

| | | | |
|---|---|---|---|
| WO | WO 2005/072740 | 8/2005 | |
| WO | WO 2006/023654 | 3/2006 | |
| WO | WO 06/044775 | 4/2006 | |
| WO | WO 2006/064189 | 6/2006 | |
| WO | WO2006064189 | * 6/2006 | ........... C07D 271/10 |
| WO | WO 2006/113919 | 10/2006 | |
| WO | WO 2006/134317 | 12/2006 | |
| WO | WO 2007/016538 | 2/2007 | |
| WO | WO 2007/022073 | 2/2007 | |
| WO | WO 2007/071966 | 6/2007 | |
| WO | WO 2007/137103 | 11/2007 | |
| WO | WO 2007/137107 | 11/2007 | |
| WO | WO 2007/0138304 | 12/2007 | |
| WO | WO 2007/138311 | 12/2007 | |
| WO | WO 2007/141502 | 12/2007 | |
| WO | WO 2007/141517 | 12/2007 | |
| WO | WO 2007/141538 | 12/2007 | |
| WO | WO 2007/141545 | 12/2007 | |
| WO | WO 2007/144571 | 12/2007 | |
| WO | WO 2008/067257 | 6/2008 | |
| WO | WO 2008/073865 | 6/2008 | |
| WO | WO 2008/099221 | 8/2008 | |
| WO | WO 2008/129319 | 10/2008 | |
| WO | WO 2008/134690 | 11/2008 | |
| WO | WO 2008/134693 | 11/2008 | |
| WO | WO 2009/011285 | 1/2009 | |
| WO | WO 2009/016462 | 2/2009 | |

OTHER PUBLICATIONS

Arulmozhi, D. K. et al. "Metabolic effects of various antidiabetic and hypolipidaemic agents on a high-fat diet and multiple low-dose streptozocin (MLDS) mouse model of diabetes" *Journal of Pharmacy and Pharmacology*, 2008, pp. 1167-1173, vol. 60.

Fujii, N. et al. "Ablation of AMP-Activated Protein Kinase α2 Activity Exacerbates Insulin Resistance Inducted by High-Fat Feeding of Mice" *Diabetes*, Nov. 2008, pp. 2958-2966, vol. 57.

Hubbard, C. E. et al. "A highly efficient route to enantiomerically pure L-N-Bz-Pmp (t-Bu)$_2$-OH and incorporation into a peptide-based protein tyrosine phosphatase inhibitor" *Bioorganic & Medicinal Chemistry Letters*, 2008, pp. 679-681, vol. 18.

Xu, Y. et al. "Preparation of New Wittig Reagents and Their Application to the Synthesis of α,β-Unsaturated Phosphonates" *J. Org. Chem.*, 1996, pp. 7697-7701, vol. 61.

Morise, X. et al. "New syntheses of 1-chioroalkylyphosphinates" *J. Chem. Soc.*, 1996, pp. 2179-2185, vol. 1.

Boyd, E. A. et al. "Facile Synthesis of Phosphorus-containing Heterocycles" *Tetrahedron Letters*, 1996, pp. 5425-5426, vol. 37, No. 30.

Ando, K. "Convenient Preparations of (Diphenylphosphono)acetic Acid Esters and the Comparison of the Z-Selectivities of Their Horner-Wadsworth-Emmons Reaction with Aldehydes Depending on the Ester Moiety" *J. Org. Chem.*, 1999, pp. 8406-8408, vol. 64.

Perumal, S. K. et al. "Synthesis and Evaluation of Ketophosph(on)ates as β-Lactamase Inhibitors" *J. Org. Chem.*, 2000, pp. 4778-4785, vol. 71.

Bonnaventure, I. et al. "Probing the Importance of the Hemilabile Site of Bis(phosphine) Monoxide Ligands in the Copper-Catalyzed Addition of Diethylzinc to N-Phosphinoylimines: Discovery of New Effective Chiral Ligands" *J. Org. Chem.*, 2008, pp. 6330-6340, vol. 73.

Jacobsen, M. F. et al. "Efficient N-Arylation and N-Alkenylation of the Five DNA/RNA Nucleobases" *J. Org. Chem.*, 2006, pp. 9183-9190, vol. 71.

Monzillo, L. U. et al. "Evaluation of Insulin Sensitivity in Clinical Practice and in Research Settings" *Nutrition Reviews*, Dec. 2003, pp. 397-412, vol. 61, No. 12.

Funato, H. et al. "Enhanced Orexin Receptor-2 Signaling Prevents Diet-Induced Obesity and Improves Leptin Sensitivity" *Cell Metabolism*, Jan. 7, 2009, pp. 64-76, vol. 9.

Green, K. "Trimethylaluminium Promoted Conjugate Additions of Dimethylphosphite to α, β-Unsaturated Esters and Ketones" *Tetrahedron Letters*, 1989, pp. 4807-4810, vol. 30, No. 36.

Ordonez, M. et al. "An overview of stereoselective synthesis of α-aminophosphonic acids and derivatives" *Tetrahedron*, 2009, pp. 17-49, vol. 65.

Bennett, S. N. L. et al. "New syntheses of arylphosphinic acids from the reaction of ethyl diethoxymethylphosphinate with aryl bromides and phenols" *J. Chem. Soc. Perkin Trans*, 1995, pp. 1145-1151, vol. 1.

Chandrasekhar, S. et al. "Solvent and Catalyst Free Three-component Coupling of Carbonyl Compounds, Amines and Triethyiphosphite; a new Synthesis of α-Amino-phosphonates" *Synlett*, 2003, pp. 505-506, vol. 4.

STN CA Caesar Accession No. 1086, 2006, pp. 1-2, XP-002733266.

* cited by examiner

INHIBITORS OF DIACYLGLYCEROL O-ACYLTRANSFERASE 1 (DGAT-1) AND USES THEREOF

CROSS REFERENCE TO RELATED APPLICATIONS

This application is a continuation U.S. application Ser. No. 14/628,373, filed Feb. 23, 2015, now U.S. Pat. No. 9,340,566, which is a divisional of U.S. application Ser. No. 13/458,452, filed Apr. 27, 2012, now U.S. Pat. No. 8,962,618, which is a continuation of U.S. application Ser. No. 13/256,952, filed Sep. 16, 2011, now abandoned, which is the U.S. national stage application of International Patent Application No. PCT/US2010/027889, filed Mar. 19, 2010, which claims the benefit of U.S. Provisional Application Ser. No. 61/162,170, filed Mar. 20, 2009, the disclosures of which are hereby incorporated by reference in their entireties, including all figures, tables and amino acid or nucleic acid sequences.

BACKGROUND

Obesity is a chronic disease that has reached global epidemic proportions with over 1 billion adults being overweight (BMI 25-29.9) or obese (BMI>30). In the U.S.A. alone, the number of adults who are either overweight or obese is estimated to be over 150 million and is still on the rise. Currently marketed therapies (orlistat, sibutramine) have demonstrated sub-optimal efficacy (only 5-10% weight loss when used in combination with diet and exercise plans) and/or poor tolerability profiles. More recently, Sanofi Aventis' CB 1 receptor antagonist, rimonabant, was withdrawn from the market due to adverse psychiatric side effects. The success of future obesity treatments will depend on their ability to elicit sustained and robust weight loss with improved safety/tolerability profiles.

Obesity (BMI>30) is the long term consequence of an imbalance between energy intake and energy expenditure (Hill et al., 2000). Further, obesity is associated with decreased life span due to numerous co-morbidities that include coronary artery disease, hypertension, stroke, diabetes, hyperlipidemia, osteoarthritis and some cancers. Adiposity is a hallmark of obesity that results from the excessive deposition of the energy storage molecule triacylglycerol (TAG) in all tissues as well as an increase in overall adipose tissue mass due to increased adipocyte size and number. Increases in intracellular TAG and/or TAG precursors in non-adipocyte cell types, adipocyte invasion of non-adipose tissues, and increase in adipose mass are the causative factors of co-morbidities associated with obesity (Van Herpen et al., 2008). Recent studies suggest that the inhibition of diacylglycerol O-acyltransferase 1 (DGAT-1) may be an effective strategy to treat obesity and obesity associated co-morbidities (Chen et al., 2005; Shi et al., 2004).

DGATs are membrane-bound enzymes that catalyze the terminal step of TAG biosynthesis (Yen et al., 2008). Two enzymes, which catalyze the acylation of diacylglycerol (DAG) to form TAG, have been identified and are designated DGAT-1 and DGAT-2. Importantly, the DGAT-1 and DGAT-2 enzymes have no significant protein sequence homology. In addition to catalyzing the acylation of DAG to form TAG, DGAT-1 has also been shown to catalyze the acylation of monoacylglycerol to form DAG (Yen et al., 2005). DGAT-1 and DGAT-2 null mice have been generated and extensively characterized (Smith et al., 2000; Stone et al., 2004). In detail, DGAT-2 null mice are lipopenic and die soon after birth from reductions in substrates for energy metabolism and from impaired permeability barrier function. In contrast, DGAT-1 mice are fertile and viable with a normal life span and do not become obese when fed a TAG rich diet. DGAT-1 null mice exhibit both reduced postprandial plasma TAG levels and increased energy expenditure, but have normal levels of circulating free fatty acids. Conversely, transgenic mice that over-express DGAT-1 in adipose tissue are predisposed to obesity when fed a TAG rich diet and have elevated levels of circulating free fatty acids (Chen et al., 2002).

In humans, DGAT-1 is highly expressed in several tissue types that are relevant to obesity, such as intestine, liver and adipose (Yen et al., 2008). Further, DGAT-1 is predominantly localized to the lumen of the endoplasmic reticulum (Yamazaki et al., 2005). Thus, there are several sites of action for a DGAT-1 inhibitor that can lead to both a reduction in adiposity and body weight. First, blocking DGAT-1 activity in the intestine or liver will inhibit the export of chylomicron and VLDL particles, respectively, thereby reducing peripheral TAG deposition that originates either from dietary TAG re-esterification or from de novo lipogenesis. Second, blocking DGAT-1 activity in adipose tissue will decrease both adipocyte size and number. In both cases, non-esterified fatty acids will be mobilized for use as an energy source rather than used for storage. DGAT-1 inhibition may also generate a peripheral satiety signal resulting in an anorexigenic effect. The phenotype of the DGAT-1 null mice, coupled with DGAT-1's role in human whole body TAG homeostasis, provides a compelling rationale for the investigation of DGAT-1, as a target for the treatment of obesity. Recently, the in vivo pharmacology of a potent orally bioavailable DGAT-1 inhibitor was disclosed (Zhao et al., 2008). Proof of concept studies in rodent models of obesity with this inhibitor demonstrated target engagement, weight loss and reductions in adiposity. This inhibitor showed high oral bioavailability and high systemic exposure.

High systemic exposure of a DGAT-1 inhibitor can potentially result in undesirable side effects such as reduced lactation in nursing females, reduced sebum production, and exacerbation of myocardial injury during ischemia. In detail, human milk TAGs are a major source of nutrition to the nursing infant and systemic inhibition of DGAT-1 would reduce milk TAG production. Female DGAT-1 null mice are unable to nurse their pups due to reduced lactation. Triglycerides are also a major component of human sebum, which is an important skin lubricant. Systemic inhibition of DGAT-1 would reduce sebum production and may result in skin and hair disorders as observed in DGAT-1 null mice. Finally, the systemic inhibition of DGAT-1 could substantially increase free fatty acid availability and utilization by the heart. During ischemia, the utilization of a less efficient fuel source such as fatty acids rather than glucose may enhance myocardial injury.

One approach to improve the therapeutic index of DGAT-1 inhibitors is to exclusively target DGAT-1 expressed in the enterocyte by restricting drug exposure primarily to enterocytes. DGAT-1 inhibitors with low systemic exposure and good oral bioavailability specifically targeted to enterocytes would avoid safety issues potentially associated with compounds that reach high levels in the systemic circulation.

SUMMARY OF THE INVENTION

The invention pertains to use of DGAT-1 inhibitors to treat and/or prevent overweight, obesity and the dyslipidemia associated with it. Because of the mechanism and specific targeting to enterocytes of the DGAT-1 inhibitors of the invention, other conditions also can be ameliorated, reduced or avoided. These conditions include high postprandial triglycerides (very common in diabetes) or diet- or obesity-related hypertriglyceridemia, cardiovascular risk associated with excessive triglycerides, and insulin resistance and glucose intolerance (e.g., improved insulin sensitivity due to reduced deposition of liver and skeletal muscle fat) seen in overweight patients, those with diabetes or other glucose metabolic disorders such as Syndrome X, polycystic ovary or other disorders.

The DGAT-1 inhibitor compounds and compositions disclosed herein primarily target enterocytes lining the intestinal walls. Thus, the disclosed compounds can be administered orally and are taken up readily into enterocytes; however, compounds of the invention are not readily exported from the enterocytes into the systemic circulation. This results in low systemic exposure to the compounds disclosed herein and reduced risk of systemic side effects associated with general systemic DGAT-1 inhibition.

DETAILED DESCRIPTION

DEFINITIONS

For a variable that occurs more than one time in any substituent, its definition on each occurrence is independent of its definition at every other occurrence. Combinations of substituents are permissible only if such combinations result in stable compounds. Stable compounds are compounds, which can be isolated in a useful degree of purity from a reaction mixture. Additionally, as used in the specification and the appended claims, unless specified to the contrary, the following terms have the meaning indicated below.

The term "alkyl" refers to a straight or branched or cyclic chain hydrocarbon radical with only single carbon-carbon bonds. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. Alkyl groups are $C_1$-$C_{12}$ and include alkyl groups that are $C_1$-$C_8$ in some embodiments.

The term "aryl" refers to aromatic groups which have 5-14 ring atoms and at least one ring having a conjugated pi electron system and includes carbocyclic aryl, heterocyclic aryl and biaryl groups, all of which may be optionally substituted.

Carbocyclic aryl groups are groups which have, in various embodiments, 6-10 or 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups which have, in various embodiments, 5-10 or 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl.

The term "optionally substituted" or "substituted" includes groups substituted by one to six substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower arylalkyloxyalkyl.

"Substituted aryl" and "substituted heteroaryl" refers to aryl and heteroaryl groups substituted with 1-3 substituents. These substituents are selected from the group consisting of lower alkyl, lower alkoxy, lower perhaloalkyl, halo, hydroxy, and amino.

The term "-aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "alkylaryl-" refers to an aryl group substituted with an alkyl group. "Lower alkylaryl-" refers to such groups where alkyl is lower alkyl.

The term "lower" referred to herein in connection with organic radicals or compounds respectively defines such as with up to and including 10, in one aspect up to and including 6, and in another aspect one to four carbon atoms. Such groups may be straight chain, branched, or cyclic.

The term "cyclic alkyl" or "cycloalkyl" refers to alkyl groups that are cyclic of 3 to 10 carbon atoms, and in one aspect are 3 to 6 or 3 to 8 carbon atoms. Suitable cyclic groups include norbornyl and cyclopropyl. Such groups may be substituted.

The term "heterocyclic", "heterocyclic alkyl" or "heterocycloalkyl" refers to cyclic groups of 3 to 10 atoms, and in one aspect are 3 to 6 atoms, containing at least one heteroatom, in a further aspect are 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The terms "arylamino" (a), and "aralkylamino" (b), respectively, refer to the group —NRR' wherein respectively, (a) R is aryl and R' is hydrogen, alkyl, aralkyl, heterocycloalkyl, or aryl, and (b) R is aralkyl and R' is hydrogen, aralkyl, aryl, alkyl or heterocycloalkyl.

The term "acyl" refers to —C(O)R where R is alkyl, heterocycloalkyl, or aryl.

The term "carboxy esters" refers to —C(O)OR where R is alkyl, aryl, aralkyl, cyclic alkyl, or heterocycloalkyl, all optionally substituted.

The term "carboxyl" refers to —C(O)OH.

The term "oxo" refers to =O in an alkyl or heterocycloalkyl group.

The term "amino" refers to —NRR' where R and R' are independently selected from hydrogen, alkyl, aryl, aralkyl and heterocycloalkyl, all except H are optionally substituted; and R and R' can form a cyclic ring system.

The term "-carboxylamido" refers to —CONR$_2$ where each R is independently hydrogen or alkyl.

The term "-sulphonylamido" or "-sulfonylamido" refers to —S(=O)$_2$NR$_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is an H or lower alkyl.

The term "sulphonyl" or "sulfonyl" refers to —SO$_2$R, where R is H, alkyl, aryl, aralkyl, or heterocycloalkyl.

The term "sulphonate" or "sulfonate" refers to —SO$_2$OR, where R is —H, alkyl, aryl, aralkyl, or heterocycloalkyl.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g., it is a W substituent attached to the cyclic phosphonate, it is attached at the first carbon.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g., it is a W substituent attached to the cyclic phosphonate, it is attached at the first carbon.

The term "alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched or cyclic.

The term "acyloxy" refers to the ester group —O—C(O)R, where R is H, alkyl, alkenyl, alkynyl, aryl, aralkyl, or heterocycloalkyl.

The term "aminoalkyl-" refers to the group NR$_2$-alk- wherein "alk" is an alkylene group and R is selected from —H, alkyl, aryl, aralkyl, and heterocycloalkyl.

The term "alkylaminoalkyl-" refers to the group alkyl-NR-alk- wherein each "alk" is an independently selected alkylene, and R is H or lower alkyl. "Lower alkylaminoalkyl-" refers to groups where the alkyl and the alkylene group is lower alkyl and alkylene, respectively.

The term "arylaminoalkyl-" refers to the group aryl-NR-alk- wherein "alk" is an alkylene group and R is —H, alkyl, aryl, aralkyl, or heterocycloalkyl. In "lower arylaminoalkyl-", the alkylene group is lower alkylene.

The term "alkylaminoaryl-" refers to the group alkyl-NR-aryl- wherein "aryl" is a divalent group and R is —H, alkyl, aralkyl, or heterocycloalkyl. In "lower alkylaminoaryl-", the alkyl group is lower alkyl.

The term "alkoxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or "alkyloxy-" refers to the group alkyl-O—.

The term "alkoxyalkyl-" or "alkyloxyalkyl-" refers to the group alkyl-O-alk- wherein "alk" is an alkylene group. In "lower alkoxyalkyl-", each alkyl and alkylene is lower alkyl and alkylene, respectively.

The terms "alkylthio-" and "alkylthio-" refer to the group alkyl-S—.

The term "alkylthioalkyl-" refers to the group alkyl-S-alk- wherein "alk" is an alkylene group. In "lower alkylthioalkyl-" each alkyl and alkylene is lower alkyl and alkylene, respectively.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "amido" refers to the NR$_2$ group next to an acyl or sulfonyl group as in NR$_2$—C(O)—, RC(O)—NR$^1$—, NR$_2$—S(=O)$_2$— and RS(=O)$_2$—NR$^1$—, where R and R$^1$ include —H, alkyl, aryl, aralkyl, and heterocycloalkyl.

The term "carboxamido" refers to NR$_2$—C(O)— and RC(O)—NR$^1$—, where R and R$^1$ include —H, alkyl, aryl, aralkyl, and heterocycloalkyl. The term does not include urea, —NR—C(O)—NR—.

The terms "sulphonamido" or "sulfonamido" refer to NR$_2$—S(=O)$_2$— and RS(=O)$_2$—NR$^1$—, where R and R$^1$ include —H, alkyl, aryl, aralkyl, and heterocycloalkyl. The term does not include sulfonylurea, —NR—S(=O)$_2$—NR—.

The terms "carboxamidoalkylaryl" and "carboxamidoaryl" refer to an aryl-alk-NR$^1$—C(O), and ar-NR$^1$—C(O)-alk-, respectively where "ar" is aryl, "alk" is alkylene, R$^1$ and R include H, alkyl, aryl, aralkyl, and heterocycloalkyl.

The terms "sulfonamidoalkylaryl" and "sulfonamidoaryl" refer to an aryl-alk-NR$^1$—S(=O)$_2$—, and ar-NR$^1$—S(=O)$_2$—, respectively where "ar" is aryl, "alk" is alkylene, R$^1$ and R include —H, alkyl, aryl, aralkyl, and heterocycloalkyl.

The term "hydroxyalkyl" refers to an alkyl group substituted with one —OH.

The term "haloalkyl" refers to an alkyl group substituted with one halo.

The term "cyano" refers to —C≡N.

The term "nitro" refers to —NO$_2$.

The term "acylalkyl" refers to an alkyl-C(O)-alk-, where "alk" is alkylene.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkylene group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "carboxylic acid moiety" refers to a compound having a carboxylic acid group (—COOH), and salts thereof, a carboxylic acid ester, or a carboxylic acid surrogate. Suitable carboxylic acid surrogates include a tetrazole group, a hydroxamic acid group, a thiazolidinedione group, an acylsulfonamide group, and a 6-azauracil. (see, e.g., The *Practice of Medicinal Chemistry*; Wemuth, C. G., Ed.; Academic Press: New York, 1996; p. 203).

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

The term "patient" means an animal.

The term "animal" includes birds and mammals, in one embodiment a mammal, including a dog, cat, cow, horse, goat, sheep, pig or human. In one embodiment the animal is a human. In another embodiment the animal is a male. In another embodiment the animal is a female.

The term "hypercholesterolemia" refers to presence of an abnormally large amount of cholesterol in the cells and plasma of the circulating blood.

The term "hyperlipidemia" or "lipemia" refers to the presence of an abnormally large amount of lipids in the circulating blood.

The term "atherosclerosis" refers to a condition characterized by irregularly distributed lipid deposits in the intima of large and medium-sized arteries wherein such deposits provoke fibrosis and calcification. Atherosclerosis raises the risk of angina, stroke, heart attack, or other cardiac or cardiovascular conditions.

The term "obesity" refers to the condition of being obese. Being obese is defined as a BMI of 30.0 or greater; and extreme obesity is defined at a BMI of 40 or greater. "Overweight" is defined as a body mass index of 25.0 to 29.9. (This is generally about 10 percent over an ideal body weight.)

The term "impaired glucose tolerance (IGT)" refers to a condition known to precede the development of overt type 2 diabetes. It is characterized by abnormal blood glucose excursions following a meal. The current criteria for the diagnosis of IGT are based on 2-h plasma glucose levels post a 75 g oral glucose test (144-199 mg/dL). Although variable from population to population studied, IGT progresses to full blown NIDDM at a rate of 1.5 to 7.3% per year, with a mean of 3-4% per year. Individuals with IGT are believed to have a 6 to 10-fold increased risk in developing NIDDM. IGT is an independent risk factor for the development of cardiovascular disease.

The term "insulin resistance" is defined clinically as the impaired ability of a known quantity of exogenous or endogenous insulin to increase whole body glucose uptake and utilization. As insulin regulates a wide variety of metabolic processes in addition to glucose homeostasis (e.g., lipid and protein metabolism), the manifestations of insulin resistance are diverse and include one or more of the following: glucose intolerance, hyperinsulinemia, a characteristic dyslipidemia (high triglycerides; low high-density lipoprotein cholesterol, and small, dense low-density lipoprotein cholesterol), obesity, upper-body fat distribution, fat accumulation in the liver (non-alcoholic fatty liver disease), NASH (non-alcoholic steatohepatitis), increased hepatic glucose output, reduced hepatic glucose uptake and storage into glycogen, hypertension, and increased prothrombotic and antifibrinolytic factors. This cluster of cardiovascular-metabolic abnormalities is commonly referred to as "The Insulin Resistance Syndrome" or "The Metabolic Syndrome" and may lead to the development of type 2 diabetes, accelerated atherosclerosis, hypertension or polycystic ovarian syndrome.

The "Metabolic Syndrome" or "Metabolic Syndrome X" is characterized by a group of metabolic risk factors in one person. They include:

Central obesity (excessive fat tissue in and around the abdomen)

Atherogenic dyslipidemia (blood fat disorders—mainly high triglycerides and low HDL cholesterol—that foster plaque buildups in artery walls)

Raised blood pressure (130/85 mmHg or higher)

Insulin resistance or glucose intolerance (the body can't properly use insulin or blood sugar)

Prothrombotic state (e.g., high fibrinogen or plasminogen activator inhibitor [−1] in the blood)

Proinflammatory state (e.g., elevated high-sensitivity C-reactive protein in the blood)

According to the present invention, "Metabolic Syndrome" or "Metabolic Syndrome X" is identified by the presence of three or more of these components:

Central obesity as measured by waist circumference:

Men: Greater than 40 inches

Women: Greater than 35 inches

Fasting blood triglycerides greater than or equal to 150 mg/dL

Blood HDL cholesterol:

Men: Less than 40 mg/dL

Women: Less than 50 mg/dL

Blood pressure greater than or equal to 130/85 mmHg

Fasting glucose greater than or equal to 110 mg/dL

The term "metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary heart disease, cardiovascular disease.

As used herein, the term "significant" or "statistically significant" means a result (i.e. experimental assay result) where the p-value is ≤0.05 (i.e. the chance of a type I error is less than 5%) as determined by an art-accepted measure of statistical significance appropriate to the experimental design.

The present invention provides compounds that are useful for treating or preventing conditions and disorders associated with DGAT in mammals, particularly humans. One aspect of the invention is directed towards the compounds represented by Formula (I), pharmaceutically acceptable salts or stereoisomers thereof, $$Q\text{-}G^1\text{-}G^2\text{-}G^3\text{-}G^4\text{-}Z \qquad \text{Formula (I)}$$

wherein

Q is $Q^1$, $Q^2$, $Q^3$, $Q^4$, $Q^5$, $Q^6$, $Q^7$, $Q^8$, or $Q^9$, as defined herein and for each of $Q^1$, $Q^2$, $Q^3$, $Q^4$, $Q^5$, $Q^6$, $Q^7$, $Q^8$, or $Q^9$, common substituents found in the structures are defined as follows:

$R^1$ is selected from the group consisting of H, $(C_1$-$C_8)$ alkyl, halo$(C_1$-$C_4)$alkyl, $(C_2$-$C_8)$alkenyl, $(C_2$-$C_8)$alkynyl, $C(O)R^a$, $OR^a$ and $NR^aR^b$; optionally, when X is $C(R^4)$, $R^a$ or $R^b$ may be combined with $R^4$ or $R^4$ may be combined with $R^1$ to form a 5-, 6- or 7-membered fused ring;

$R^a$ and $R^b$ are independently selected from the group consisting of H, $(C_1$-$C_8)$alkyl, $(C_2$-$C_8)$alkenyl, $(C_2$-$C_8)$alkynyl, fluoro$(C_1$-$C_8)$alkyl, $(C_3$-$C_8)$cycloalkyl, aryl, heteroaryl and aryl$(C_1$-$C_4)$alkyl;

$R^2$ and $R^3$ are independently selected from the group consisting of H, $(C_1$-$C_8)$alkyl, $(C_2$-$C_8)$alkenyl, $(C_2$-$C_8)$alkynyl, $C(O)R^a$, $CO_2R^a$, $C(O)NR^aR^b$, $(C_1$-$C_4)$alkylene-$OR^a$ and $(C_1$-$C_4)$perfluoroalkyl; or $R^2$ and $R^3$ may be combined to form a 3-, 4-, 5- or 6-membered spiro ring; optionally, having from 0 to 3 heteroatoms selected from the group consisting of N, O and S;

each $R^4$ is independently selected from the group consisting of H, $(C_1$-$C_8)$alkyl, $(C_2$-$C_8)$alkenyl, $(C_2$-$C_8)$alkynyl, fluoro$(C_1$-$C_8)$alkyl, aryl, aryl$(C_1$-$C_4)$alkyl, $C(O)R^a$, $CO_2R^a$ and $C(O)NR^aR^b$;

$R^6$ is an optionally substituted aryl or optionally substituted heteroaryl group, wherein the optional substituents are one or more groups selected from H, $(C_1$-$C_4)$alkyl, halo, halo$(C_1$-$C_4)$alkyl, cyano, $(C_1$-$C_4)$alkoxy, $(C_1$-$C_4)$haloalkoxy, —$C(O)_xR^a$, —$OR^a$, —$S(O)_xR^a$, —$NR^aR^b$, —$C(O)NR^aR^b$, —$NR^aC(O)R^b$, —$NR^aCO\,NR^aR^b$, —$S(O)_2NR^aR^b$ or —$NR^aS(O)_2NR^aR^b$ where x is an integer of 1 or 2;

T is N, CH or CMe;

$R^8$ is independently selected from halo, $(C_1$-$C_6)$alkyl, $(C_2$-$C_6)$alkenyl, aryl, heteroaryl, $(C_3$-$C_8)$cycloalkyl, cyano, $(C_1$-$C_6)$haloalkyl, $(C_1$-$C_6)$haloalkoxy, —$OR^a$, —O—$C(O)(R^a)$, —$S(R^a)$, —$S(O)(R^b)$, —$S(O)_2(R^b)$, —$C(O)(R^a)$, —$C(O)(OR^a)$, —$N(R^a)_2$, —$N(R^a)$—$C(O)(R^a)$, —$C(O)N(R^a)_2$, —$S(O)_2N(R^a)_2$, —$(CR^aR^b)_tOR^a$, —$(CR^aR^b)_t$—O—$C(O)(R^a)$, —$(CR^aR^b)_tS(R^a)$, —$(CR^aR^b)_tS(O)(R^b)$, —$(CR^aR^b)_tS(O)_2(R^b)$, —$(CR^aR^a)_tC(O)(R^a)$, —$(CR^aR^b)_tC(O)(OR^a)$, —$(CR^aR^b)_tN(R^a\ R^b)$ —$(CR^aR^b)_tN(R^a)$—$C(O)(R^a)$, —$(CR^aR^b)_tC(O)N(R^a)_2$, —$(CR^aR^a)_tS(O)_2N(R^a)_2$ or —$(CR^aR^b)_tR^a$ and wherein t is an integer of 1, 2, 3, or 4;

$Q^1$ is

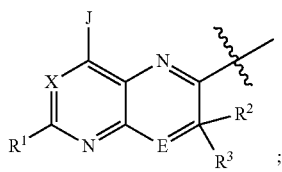

wherein J is selected from —$NR^aR^b$ or —$OR^a$;

X is selected from the group consisting of $C(R^4)$ and N; optionally, when X is $C(R^4)$, $R^a$ or $R^b$ may be combined with $R^4$ or $R^4$ may be combined with $R^1$ to form a 5-, 6- or 7-membered fused ring;

E is selected from the group consisting of O and S;

$Q^2$ is

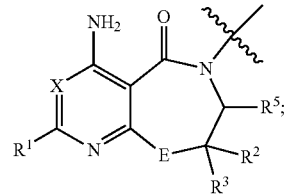

$R^5$ is H or $(C_1$-$C_4)$alkyl;

X is N or $C(R^4)$ and when X is $C(R^4)$, $R^4$ may be combined with $R^1$ to form a 5-, 6- or 7-membered fused ring;

$R^2$ and $R^3$ are as defined above or may be combined with $R^5$ to form a 3-, 4-, 5- or 6-membered spiro ring; optionally, having from 0 to 3 heteroatoms selected from the group consisting of N, O and S;

$Q^3$ is

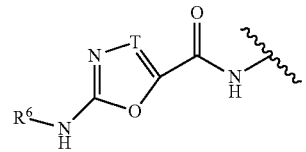

$Q^4$ is

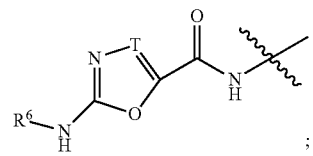

$Q^5$ is

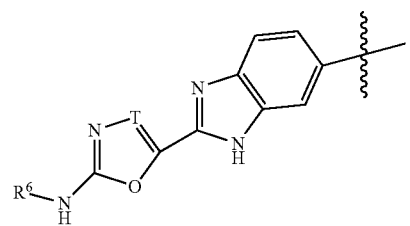

$Q^6$ is $R^7(V)_nC(O)(NH)_m$—;

$R^7$ is $(C_1$-$C_8)$alkyl, aryl, heteroaryl or $(C_3$-$C_8)$cycloalkyl; wherein each of the aryl, heteroaryl and cycloalkyl is independently substituted with 1, 2, 3, 4, or 5 substituents independently selected from the group consisting of $(C_1$-$C_8)$alkyl, $(C_2$-$C_8)$alkenyl, $(C_2$-$C_8)$alkynyl, —CN, halogen, ethylenedioxy, methylenedioxy, haloalkyl, —$OR^a$, —O—$C(O)(R^a)$, —$S(R^a)$, —$S(O)(R^b)$, —$S(O)_2(R^b)$, —$C(O)(R^a)$, —$C(O)(OR^a)$, —$N(R^a)_2$, —$N(R^a)$—$C(O)(R^a)$, —$C(O)N(R^a)_2$, —$S(O)_2N(R^a)_2$, —$(CR^aR^b)_tOR^a$, —$(CR^aR^b)_t$—O—$C(O)(R^a)$, —$(CR^aR^b)_tS(R^a)$, —$(CR^aR^b)_tS(O)(R^b)$, —$(CR^aR^b)_tS(O)_2(R^b)$, —$(CR^aR^a)_tC(O)(R^a)$, —$(CR^aR^b)_tC$ (O)(OR$^a$), —(CR$^a$R$^b$)$_t$N(R$^a$ R$^b$) —(CR$^a$R$^b$)$_t$N(R$^a$)—C(O)(R$^a$), —(CR$^a$R$^b$)$_t$C(O)N(R$^a$)$_2$, —(CR$^a$R$^a$)$_t$S(O)$_2$N(R$^a$)$_2$ and —(CR$^a$R$^b$)$_t$R$^a$, V is —NH—, —O—, —(CR$^a$R$^b$)$_t$—;
where t is an integer of 1, 2, 3, or 4;
m is 0 or 1;
n is 0 or 1;
Q$^7$ is

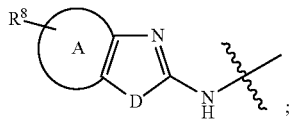

wherein D is O, NR$^c$, or S; and
A is a fused ring selected from an aromatic 6-membered ring containing 0 or 2 N atoms;
the number of R$^8$ substituents on A ring may be 0, 1 or 2 and when two of said R$^8$ substituents are: a) found on A ring; b) (C$_1$-C$_6$)alkyl and c) attached to adjacent carbon atoms of the Ring A, they may be joined together to form a 5 to 7-membered carbocyclic ring; and
R$^c$ is H or (C$_1$-C$_6$)alkyl, hydroxyl(C$_2$-C$_6$)alkyl;
Q$^8$ is

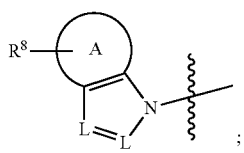

L is N or C(R$^8$); and
the number of R$^8$ substituents on A ring may be 0, 1, 2 or 3 and when two of said R$^8$ substituents are: a) found on A ring; b) (C$_1$-C$_6$)alkyl and c) attached to adjacent carbon atoms of the Ring A, they may be joined together to form a 5- to 7-membered carbocyclic ring containing 0, 1, 2 or 3 heteroatoms selected from O, N, S; or
Q$^9$ is a [5,5], [5,6], [6,5] and [6,6] bicylic heterocycle containing 1 to 4 N atoms where G$^1$ is connected through one of the ring N atoms;
G$^1$ and G$^3$ are independently selected from the group consisting of cyclo(C$_3$-C$_8$)alkylene, heterocyclo(C$_3$-C$_8$)alkylene, arylene and heteroarylene, optionally substituted with one or two groups independently selected from halo, (C$_1$-C$_6$)alkyl, (C$_2$-C$_6$)alkenyl, (C$_1$-C$_6$)alkoxy, cyano, (C$_1$-C$_6$)haloalkyl, (C$_1$-C$_6$)haloalkoxy, (C$_1$-C$_4$)perfluoroalkyl; —N(R$^a$R$^b$), —N(R$^a$)—C(O)(R$^a$), —C(O)N(R$^a$)$_2$, —S(O)$_2$N(R$^a$)$_2$ —S(O)$_2$(R$^b$) and —C(O)(R$^a$).

G$^2$ is selected from the group consisting of a bond, (C$_1$-C$_4$)alkylene, (C$_2$-C$_4$)alkenylene, O, N(R$^a$)C(O), S and S(O)$_2$;
G$^4$ is -X—Y—
wherein X is selected from null, O, NH, CO, CHOH, S or S(O)$_2$; and Y is selected from (C$_1$-C$_4$)alkylene, (C$_3$-C$_8$)-cycloalkylene or (C$_3$-C$_8$)-heterocycloalkylene, —CH(R$^9$)C(R$^{10}$R$^{11}$)— or —N(R$^9$)C(R$^{10}$R$^{11}$)—
wherein
R$^{10}$ and R$^{11}$ are both hydrogen, and R$^9$ is hydrogen, (C$_1$-C$_6$)alkyl, (C$_1$-C$_6$)alkoxy, (C$_2$-C$_6$)alkenyl, phenoxy-(C$_2$-C$_6$)alkyl, 1-methyl-1H-indol-3-yl, bis[(C$_1$-C$_6$)alkyl]amino-(C$_2$-C$_6$)alkyl, 1-piperidinyl-(C$_2$-C$_6$)alkyl, 1-pyrrolidinyl-(C$_2$-C$_6$)alkyl, or 1-morpholinyl-(C$_2$-C$_6$) alkyl;
or R$^{10}$ and R$^{11}$ are both hydrogen and R$^9$ is R$^{12}$(CH$_2$)$_m$, where m is 0 to 3, and R$^{12}$ is phenyl optionally substituted with one or more halogen, hydroxy, (C$_1$-C$_6$)alkyl, (C$_1$-C$_6$)alkoxy, trifluoromethyl or cyano;
or R$^{10}$ and R$^{11}$ are both hydrogen and R$^9$ is R$^{12}$(CH$_2$)$_m$, where m is 0 to 3, and R$^{12}$ is 2-pyridinyl, 3-pyridinyl, or 4-pyridinyl, each of which is optionally substituted with halogen, (C$_1$-C$_6$)alkyl, (C$_1$-C$_6$)alkoxy, trifluoromethyl or cyano; or R$^9$ is hydrogen, and R$^{10}$ and R$^{11}$ together with the carbon atom to which they are attached, form a three to five-membered ring, with 0 to 2 heteroatoms independently selected from O, S or N; or R$^{10}$ is hydrogen, and R$^9$ and R$^{11}$ together with the two carbon atoms to which they are attached, form a three- to six-membered ring with 0 to 2 heteroatoms independently selected from O, S or N;
Z is Z$^1$ or Z$^2$ as defined herein;
Z$^1$ is

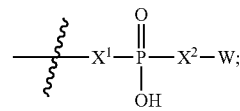

X$^1$ and X$^2$ are independently selected from null, (C(R$^a$R$^b$))$_n$, O, NR$^a$, S or CO and n is 0 or 1; W is selected from H, (C$_1$-C$_6$)alkyl, aryl, heteroaryl or (C$_3$-C$_8$)cycloalkyl; wherein each of the alkyl, aryl, heteroaryl and cycloalkyl is independently substituted with 1, 2, 3, 4, or 5 substituents independently selected from the group consisting of (C$_1$-C$_6$)alkyl, (C$_2$-C$_8$)alkenyl, (C$_2$-C$_8$)alkynyl, —CN, halogen, ethylenedioxy, methylenedioxy, haloalkyl, —OR$^a$, —O—C(O)(R$^a$), —S(R$^a$), —S(O)(R$^b$), —S(O)$_2$(R$^b$), —C(O)(R$^a$), —C(O)(OR$^a$), —N(R$^a$)$_2$, —N(R$^a$)—C(O)(R$^a$), —C(O)N(R$^a$)$_2$, —S(O)$_2$N(R$^a$)$_2$, —(CR$^a$R$^b$)$_t$OR$^a$, —(CR$^a$R$^b$)$_t$—O—C(O)(R$^a$), —(CR$^a$R$^b$)$_t$S(R$^a$), —(CR$^a$R$^b$)$_t$S(O) (R$^b$), —(CR$^a$R$^b$)$_t$S(O)$_2$(R$^b$), —(CR$^a$R$^a$)$_t$C(O)(R$^a$), —(CR$^a$R$^b$)$_t$C(O)(OR$^a$), —(CR$^a$R$^b$)$_t$N(R$^a$R$^b$)—(CR$^a$R$^b$)$_t$N(R$^a$)—C(O)(R$^a$), —(CR$^a$R$^b$)$_t$C(O)N(R$^a$)$_2$, —(CR$^a$R$^a$)$_t$S(O)$_2$N(R$^a$)$_2$ and —(CR$^a$R$^b$)$_t$R$^a$, —(CR$^a$R$^b$)$_t$P(O)(OH)$_2$, and —(CR$^a$R$^b$)$_t$P(O)(OH)(R$^a$), wherein t is an integer of 1, 2, 3, or 4;

X$^1$ and X$^2$ may be combined to form a 5-, 6- or 7-membered ring having from 0 to 3 heteroatoms selected from the group consisting of NR$^a$, O and S; or X$^1$ or X$^2$ may be combined with W to form a 5-, 6- or 7-membered fused ring having from 0 to 3 heteroatoms selected from the group consisting of NR$^a$, O and S;
Z$^2$ is Z$^1$, H, —OH, CO$_2$R$^a$ or —C(O)N(R$^a$)$_2$;
with a proviso that when X$^2$ is O and Q is Q$^1$, Q$^2$, Q$^3$, Q$^4$, Q$^5$, Q$^6$, Q$^7$ or Q$^9$, then X$^1$ is not (C(R$^a$R$^b$))$_n$ and when Q is Q$^8$ then Z is Z$^2$ and Z$^2$ is Z$^1$, H, —OH, CO$_2$R$^a$ or —C(O)N(R$^a$)$_2$.

Another aspect of the invention provides for pharmaceutically acceptable salts of the compounds of Formula (I), in addition to those discussed in the definitions section of this application. Such salts include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate persulfate, 3-phenylpropionate, picrate, pivalate, propionate, succinate, sulfonate, tartrate, thiocyanate, tosylate, and undecanoate. Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate and diamyl sulfates; long chain halides such as decyl, lauryl, myristyl and strearyl chlorides, bromides, and iodides; aralkyl halides like benzyl and phenethyl bromides and others.

Another aspect of the invention provides pharmaceutical compositions formed by combining the compounds of this invention with pharmaceutically acceptable carriers, vehicles or diluents. These pharmaceutically acceptable compositions can, then, be administered in a variety of dosage forms such as tablets, powders, lozenges, syrups, injectable solutions and the like. These pharmaceutical compositions can, if desired, contain additional ingredients such as flavorings, binders and/or excipients.

Thus, one aspect of the invention provides pharmaceutical composition for oral administration. For example, tablets containing various excipients such as sodium citrate, calcium carbonate and/or calcium phosphate, may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions comprising the aforementioned excipients, disintegrants and/or lubricating agents may also be employed as fillers in soft and hard filled gelatin capsules. Additionally, materials such as lactose or milk sugar and high molecular weight polyethylene glycols can also be utilized in the preparation of soft or hard capsules disclosed herein. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof. Tablets and capsules disclosed herein can also be formulated with enteric coatings known to those skilled in the art.

For parenteral administration, solutions comprising compounds disclosed herein can be formulated in oils (such as sesame or peanut oil), aqueous propylene glycol, or in sterile aqueous solutions. Aqueous solutions should be suitably buffered, if necessary, and the liquid diluent first rendered isotonic with sufficient saline or glucose. Compounds formulated as discussed herein are suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds or compositions of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

Methods of preparing various pharmaceutical compositions with a certain amount of active ingredient are known, or will be apparent in light of this disclosure, to those skilled in this art. Methods of preparing pharmaceutical compositions are known to those skilled in the art (see Remington's Pharmaceutical Sciences, Mack Publishing Company, Easton, Pa., 19th Edition (1995)).

In another aspect of the invention, methods of inhibiting or reducing the activity of DGAT-1 in enterocytes are provided that comprise contacting an enterocyte with a composition comprising a compound of Formula (I), or a pharmaceutically acceptable salt of a compound of Formula (I). In this aspect of the invention, the enterocyte is contacted with an amount of the composition sufficient to inhibit DGAT-1 activity within the cell. This method can be conducted in vitro or in vivo.

The terms "treating", "treated", or "treatment" as employed herein includes palliating, slowing progression and/or reducing symptoms associated with a disease, such as obesity, insulin resistance syndrome, Type 2 diabetes, or adiposity. The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

In another aspect of the invention, methods of treating a disease or condition amenable to treatment via DGAT-1 inhibition are provided. These methods comprise administering to a mammal a therapeutically effective amount of a compound of Formula (I), or a pharmaceutically acceptable salt of the compound, either alone or in combination with an anti-diabetic agent as described above. Conditions that can be treated in this aspect of the invention include Type 2 diabetes, insulin resistance syndrome, obesity, impaired glucose tolerance, hyperglycemia, high postprandial triglycerides (very common in diabetes) or diet- or obesity-related hypertriglyceridemia, cardiovascular risk associated with excessive triglycerides, and insulin resistance and glucoseintolerance (e.g., improved insulin sensitivity due to reduced deposition of liver and skeletal muscle fat) seen in overweight patients, those with diabetes or other glucose metabolic disorders such as Syndrome X, polycystic ovary disease or other disorders such as diabetic complications that arise from obesity.

The present invention also relates to therapeutic methods for treating the above described conditions in a mammal, including a human, wherein a compound of Formula (I) is administered as part of an appropriate dosage regimen designed to obtain the benefits of the therapy. The appropriate dosage regimen, the amount of each dose administered and the intervals between doses of the compound will depend upon the compound of Formula (I) of this invention being used, the type of pharmaceutical compositions being used, the characteristics of the subject being treated and the severity of the conditions.

In general, an effective dosage for the compounds of the present invention is in the range of 0.01 mg/kg/day to 1000 mg/kg/day, preferably 0.01 mg/kg/day to 600 mg/kg/day of active compound (i.e., a compound of Formula (I)) in single or divided doses (for example, three doses of 200 mg/kg over the course of a day). Some variation in dosage will necessarily occur, however, depending on the condition of the subject being treated. The individual responsible for dosing will, in any event, determine the appropriate dose for the individual subject. Practitioners will appreciate that "kg" refers to the weight of the subject measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. The compounds or compositions of the present invention may be administered to a subject in need of treatment by a variety of conventional routes of administration, including orally and parenterally, (e.g., intravenously or subcutaneously). Further, the pharmaceutical compositions of this invention may be administered intranasally, as a suppository, or using a "flash" formulation, i.e., allowing the medication to dissolve in the mouth without the need to use water. The compounds are preferably delivered via a route that accesses the alimentary tract, e.g., orally or nasally.

Combination therapies utilizing compounds of Formula (I) are provided by yet another aspect of the invention. Thus, compounds of Formula (I) can be administered in combination (concomitantly or sequentially and as a single combined composition or as separate compositions that are separately administered), with anti-diabetic and/or anti-obesity agents known to those skilled in the art. Non-limiting examples of anti-obesity agents include: 1) central nervous system agents that affect neurotransmitters or neural ion channels, including antidepressants (bupropion), selective serotonin 2c receptor agonists, antiseizure agents (topiramate, zonisamide), some dopamine antagonists, and cannabinoid-1 receptor antagonists (rimonabant); 2) leptin/insulin/central nervous system pathway agents, including leptin analogues, leptin transport and/or leptin receptor promoters, ciliary neurotrophic factor (Axokine), neuropeptide Y and agouti-related peptide antagonists, proopiomelanocortin and cocaine and amphetamine regulated transcript promoters, alpha-melanocyte-stimulating hormone analogues, melanocortin-4 receptor agonists, and agents that affect insulin metabolism/activity, which include protein-tyrosine phosphatase-1B inhibitors, peroxisome proliferator activated receptor-gamma receptor antagonists, short-acting bromocriptine (ergoset), somatostatin agonists (octreotide), and adiponectin; 3) gastrointestinal-neural pathway agents, including those that increase cholecystokinin activity, increase glucagon-like peptide-1 activity (extendin 4, liraglutide, dipeptidyl peptidase IV inhibitors), and increase protein YY3-36 activity and those that decrease ghrelin activity, as well as amylin analogues (pramlintide); 4) agents that may increase resting metabolic rate ("selective" beta-3 stimulators/agonist, uncoupling protein homologues, and thyroid receptor agonists); and 5) other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis, carboxypeptidase inhibitors, indanones/indanols, aminosterols, and other gastrointestinal lipase inhibitors (ATL962). Anti-diabetic agents that can be used in the aforementioned combination therapies include, and are not limited to: insulin; sulfonylurea compounds, such as glyburide, tolbutamide, acetohexamide, tolazamide, chlorpropamide, glipizide, glimepiride or gliclazide; meglitinides, such as repaglinide or nateglinide; biguanides, such as metformin, phenformin or buformin; thiazolidinediones, such as rosigliazone, pioglitozone or troglitazone, alpha-glucosidase inhibitors, such as miglitol or asarabose; peptides or peptide analogs, such as glucagon-like peptide 1, gastric inhibitory peptide, exenatide, exendin-4, liraglutide or taspoglatide; DPP-IV inhibitors, such as vildagliptin or sitaliptin; amylin analogs, such as pramlintide; PPARα/γ ligands, such as aleglitazar, muraglitazar or tesaglitazar; SGLT (sodium-dependent glucose transporter 1) or FBPase (fructose 1,6-bisphosphatase) inhibitors, such as those disclosed in U.S. Pat. Nos. 6,967,193; 6,965,033; 6,919,322; 6,489,476; 6,399,782; or 6,110,903 each of which is hereby incorporated by reference in its entirety.

EXAMPLES

Numerous compounds of the invention have been synthesized and shown to target enterocytes and exhibit inhibition of DGAT-1. Various data are shown by way of example below. The physical characteristics of some molecules of the invention are included in Table 1 below.

TABLE 1

Elemental Analysis and Mass Spec Data of Certain Compounds of the Present Invention

| Compound Number | Structure | Elemental Analysis CHN (calcd) CHN (Found) Formula | Mass Spec MH+ |
| --- | --- | --- | --- |
| 1 | 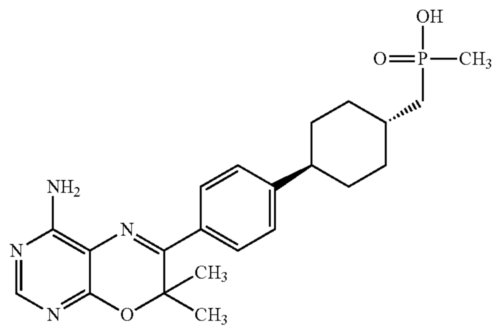 [SMILES: CC1(C)Oc2ncnc(N)c2N=C1c1ccc([C@H]2CC[C@H](CP(C)(=O)O)CC2)cc1] | C: 60.40, H: 6.91, N: 12.81<br>C: 60.81, H: 7.29, N: 12.42<br>$C_{22}H_{29}N_4O_3P + 0.5\ H_2O$ | 492 |
| 2 | 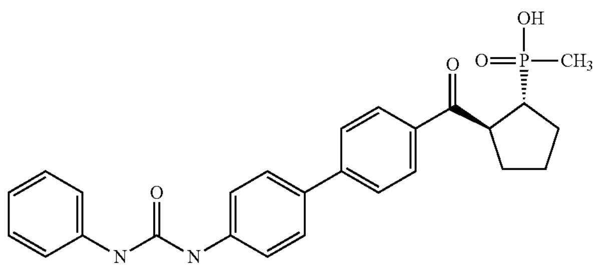 [SMILES: CP(=O)(O)[C@@H]1CCC[C@H]1C(=O)c1ccc(-c2ccc(NC(=O)Nc3ccccc3)cc2)cc1] | C: 64.99, H: 6.08, N: 5.83<br>C: 64.75, H: 6.03, N: 5.40<br>$C_{26}H_{27}N_2O_4P + 1.0\ H_2O$ | 463 |
| 3 | 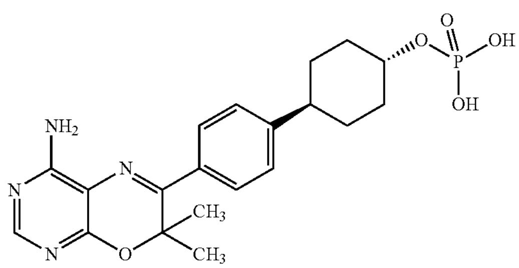 [SMILES: CC1(C)Oc2ncnc(N)c2N=C1c1ccc([C@H]2CC[C@H](OP(=O)(O)O)CC2)cc1] | C: 53.82, H: 6.59, N: 11.52<br>C: 53.55, H: 6.24, N: 11.64<br>$C_{20}H_{25}N_4O_5P + 1.0\ H_2O + 0.6\ i\text{-PrOH}$ | 433 |
| 4 | 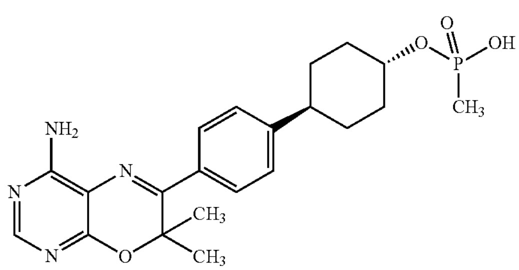 [SMILES: CC1(C)Oc2ncnc(N)c2N=C1c1ccc([C@H]2CC[C@H](OP(C)(=O)O)CC2)cc1] | C: 56.24, H: 6.52, N: 12.49<br>C: 55.76, H: 6.57, N: 12.13<br>$C_{21}H_{27}N_4O_4P + 1.0\ H_2O$ | 431 |
| 5 | 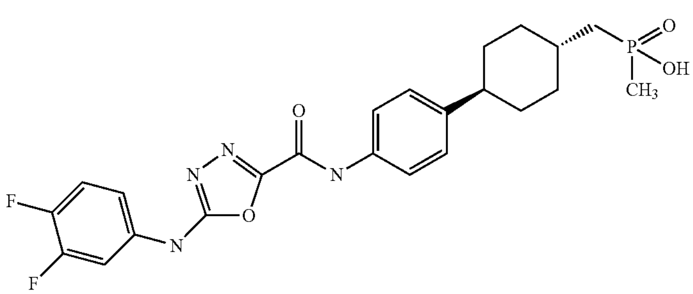 [SMILES: CP(=O)(O)C[C@H]1CC[C@H](c2ccc(NC(=O)c3nnc(Nc4ccc(F)c(F)c4)o3)cc2)CC1] | C: 55.31, H: 5.25, N: 11.22<br>C: 55.11, H: 4.87, N: 11.18<br>$C_{23}H_{25}F_2N_4O_4P + 0.5\ H_2O$ | 491 |

TABLE 1-continued

Elemental Analysis and Mass Spec Data of Certain
Compounds of the Present Invention

| Compound Number | Structure | Elemental Analysis<br>CHN (calcd)<br>CHN (Found)<br>Formula | Mass Spec MH+ |
|---|---|---|---|
| 6 | 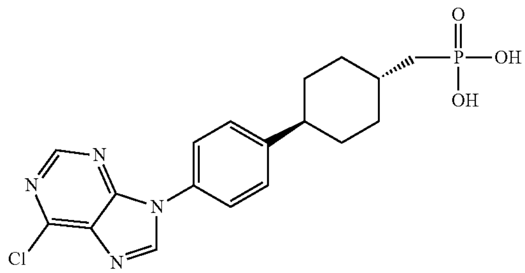 [SMILES: O=P(O)(O)C[C@H]1CC[C@H](c2ccc(-n3cnc4c(Cl)ncnc43)cc2)CC1] | C: 50.18, H: 4.90, N: 12.72<br>C: 50.13, H: 4.66, N: 12.80<br>$C_{18}H_{20}ClN_4O_3P$ + 0.6 $H_2O$<br>+<br>0.2 $CF_3CO_2H$ | 407 |
| 7 | 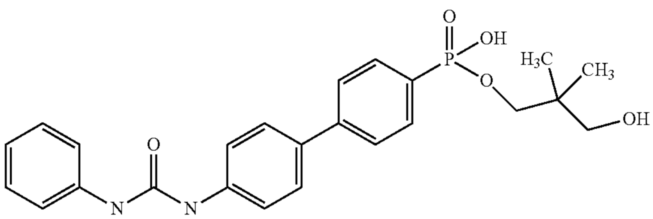 [SMILES: CC(C)(CO)COP(=O)(O)c1ccc(-c2ccc(NC(=O)Nc3ccccc3)cc2)cc1] | C: 56.93, H: 6.61, N: 6.64<br>C: 57.09, H: 6.68, N: 6.81<br>$C_{24}H_{27}N_2O_5P$ + 2.5 $H_2O$ +<br>0.4 $NH_3$ | 455 |
| 8 | 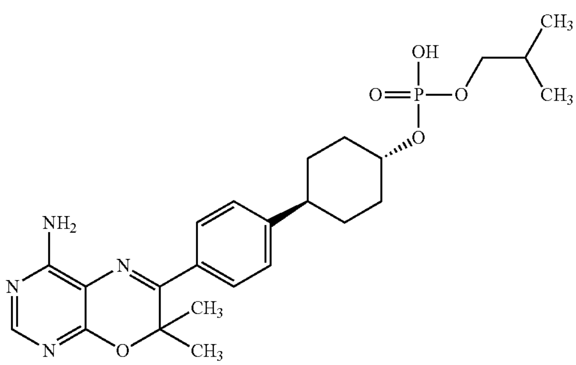 [SMILES: CC(C)COP(=O)(O)O[C@H]1CC[C@H](c2ccc(C3=Nc4c(N)ncnc4OC3(C)C)cc2)CC1] | C: 57.73, H: 6.90, N: 11.22<br>C: 57.78, H: 7.28, N: 10.79<br>$C_{24}H_{33}N_4O_5P$ + 0.6 $H_2O$ | 489 |
| 9 | 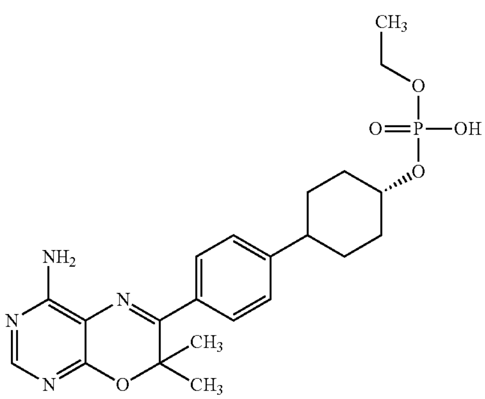 | C: 51.36, H: 6.86, N: 10.89<br>C: 50.96, H: 6.49, N: 10.60<br>$C_{22}H_{29}N_4O_5P$ + 3.0 $H_2O$ | 461 |

TABLE 1-continued
Elemental Analysis and Mass Spec Data of Certain Compounds of the Present Invention
| Compound Number | Structure | Elemental Analysis CHN (calcd) CHN (Found) Formula | Mass Spec MH+ |
|---|---|---|---|
| 10 | 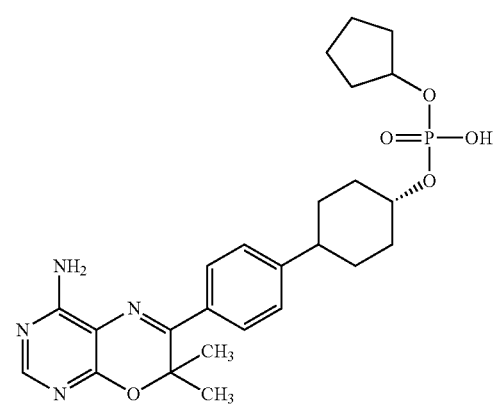 | C: 53.62, H: 7.13, N: 10.01<br>C: 53.21, H: 6.54, N: 9.84<br>$C_{25}H_{33}N_4O_5P + 3.3\ H_2O$ | 501 |
| 11 | 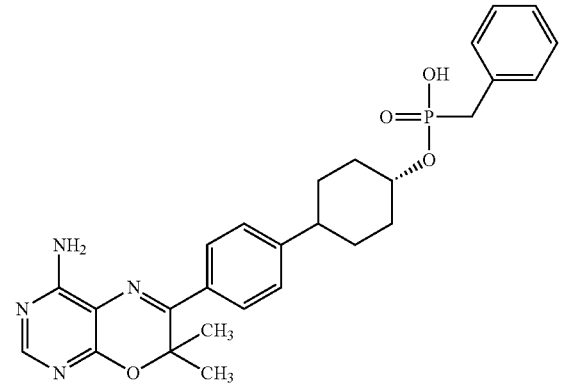 | C: 61.82, H: 6.34, N: 10.68<br>C: 61.35, H: 6.20, N: 10.65<br>$C_{27}H_{31}N_4O_4P + 1.0\ H_2O$ | 507 |
| 12 | 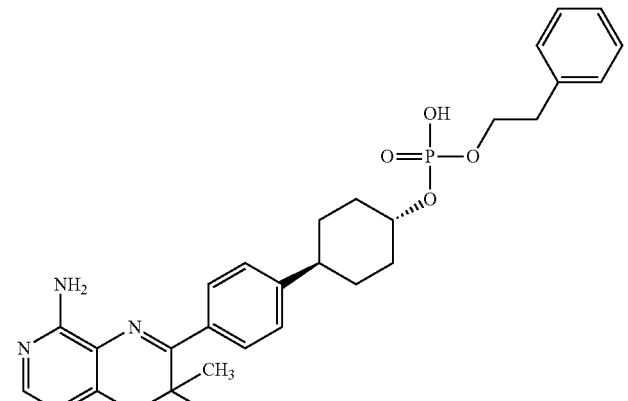 | C: 60.64, H: 6.36, N: 10.10<br>C: 60.98, H: 6.39, N: 9.62<br>$C_{28}H_{33}N_4O_5P + 1.0\ H_2O$ | 537 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
| --- | --- | --- | --- |
| 13 | 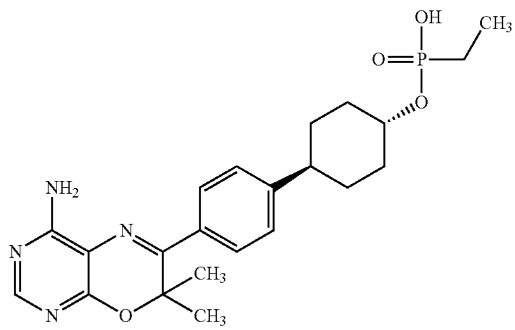 [SMILES: CCP(=O)(O)O[C@H]1CC[C@H](c2ccc(C3=Nc4c(N)ncnc4OC3(C)C)cc2)CC1] | C: 56.26, H: 6.82, N: 11.93<br>C: 56.19, H: 6.69, N: 11.76<br>$C_{22}H_{29}N_4O_4P + 1.4\ H_2O$ | 445 |
| 14 | 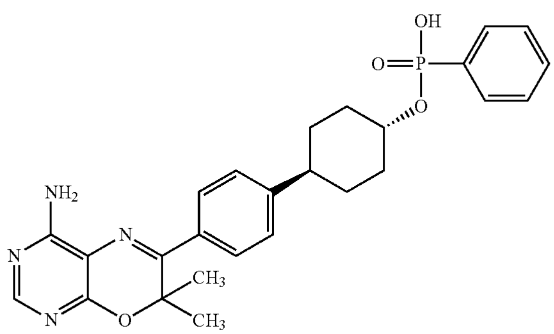 [SMILES: CC1(C)Oc2ncnc(N)c2N=C1c1ccc([C@H]2CC[C@H](OP(=O)(O)c3ccccc3)CC2)cc1] | C: 62.27, H: 6.03, N: 11.17<br>C: 61.88, H: 5.66, N: 11.02<br>$C_{26}H_{29}N_4O_4P + 0.5\ H_2O$ | 493 |
| 15 | 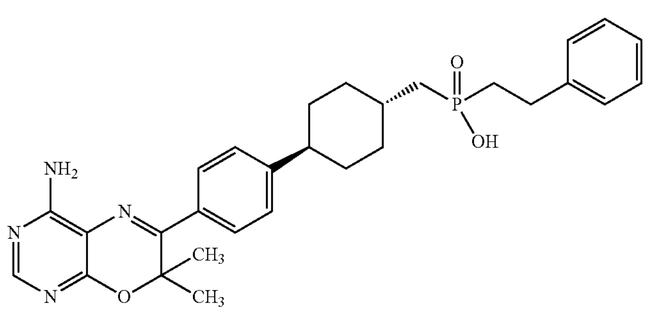 [SMILES: CC1(C)Oc2ncnc(N)c2N=C1c1ccc([C@H]2CC[C@H](CP(=O)(O)CCc3ccccc3)CC2)cc1] | C: 55.65, H: 6.67, N: 10.74<br>C: 55.98, H: 7.07, N: 11.06<br>$C_{29}H_{35}N_4O_3P + 1.6\ H_2O + 0.8\ NH_4Br$ | 519 |
| 16 | 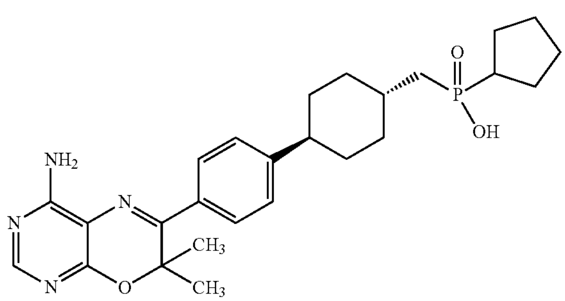 [SMILES: CC1(C)Oc2ncnc(N)c2N=C1c1ccc([C@H]2CC[C@H](CP(=O)(O)C3CCCC3)CC2)cc1] | C: 62.39, H: 7.45, N: 11.19<br>C: 62.61, H: 7.39, N: 11.40<br>$C_{26}H_{35}N_4O_3P + 1.0\ H_2O$ | 483 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
| --- | --- | --- | --- |
| 17 | 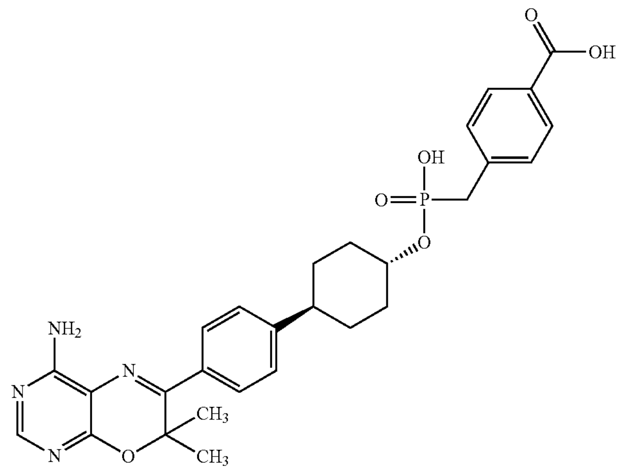 [SMILES: CC1(C)Oc2ncnc(N)c2N=C1c1ccc([C@H]2CC[C@H](OP(=O)(O)Cc3ccc(C(=O)O)cc3)CC2)cc1] | C: 58.23, H: 5.93, N: 9.70<br>C: 58.02, H: 5.61, N: 9.47<br>$C_{28}H_{31}N_4O_6P$ + 1.5 $H_2O$ | 551 |
| 18 | 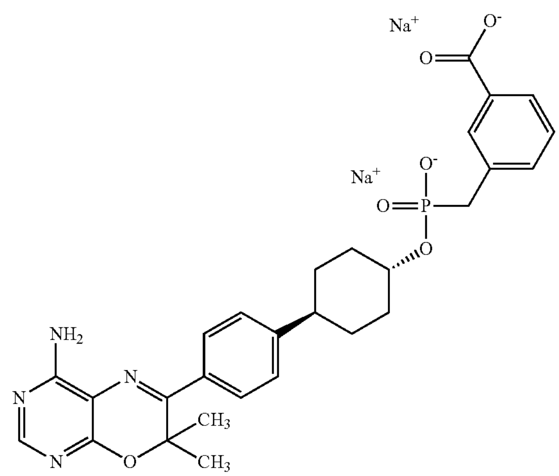 [SMILES: CC1(C)Oc2ncnc(N)c2N=C1c1ccc([C@H]2CC[C@H](OP(=O)([O-])Cc3cccc(C(=O)[O-])c3)CC2)cc1 ; [Na+] ; [Na+]] | C: 45.09, H: 4.83, N: 7.25<br>C: 44.95, H: 5.17, N: 6.98<br>$C_{28}H_{29}N_4O_6PNa_2$ +<br>4.0 $H_2O$ + 1.0 $Na_2CO_3$ | 551 |
| 19 | 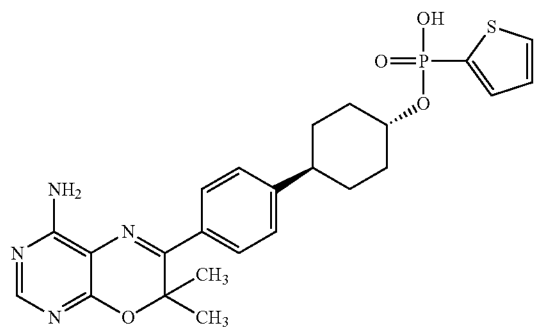 [SMILES: CC1(C)Oc2ncnc(N)c2N=C1c1ccc([C@H]2CC[C@H](OP(=O)(O)c3cccs3)CC2)cc1] | C: 57.00, H: 5.54, 11.08<br>C: 56.85, H: 5.57, N: 10.92<br>$C_{24}H_{27}N_4O_4SP$ + 0.4 $H_2O$ | 499 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
| --- | --- | --- | --- |
| 20 | 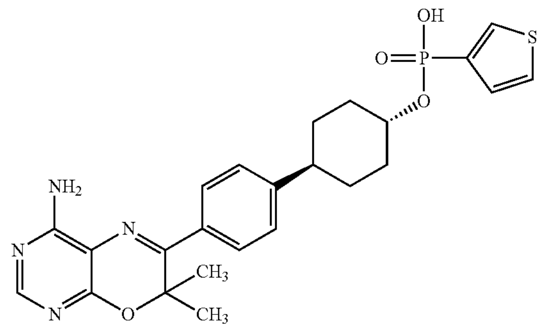 [SMILES: CC1(C)Oc2ncnc(N)c2N=C1c1ccc([C@H]2CC[C@H](OP(=O)(O)c3ccsc3)CC2)cc1] | C: 57.00, H: 5.54, N: 11.08<br>C: 57.09, H: 5.39, N: 11.13<br>$C_{24}H_{27}N_4O_4SP + 0.4 H_2O$ | 499 |
| 21 | 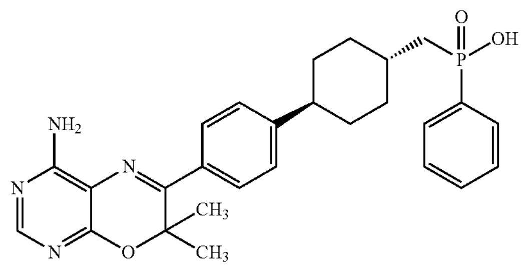 [SMILES: CC1(C)Oc2ncnc(N)c2N=C1c1ccc([C@H]2CC[C@H](CP(=O)(O)c3ccccc3)CC2)cc1] | C: 64.92, H: 6.46, N: 11.22<br>C: 64.78, H: 6.49, N: 11.03<br>$C_{27}H_{31}N_4O_3P + 0.5 H_2O$ | 491 |
| 22 | 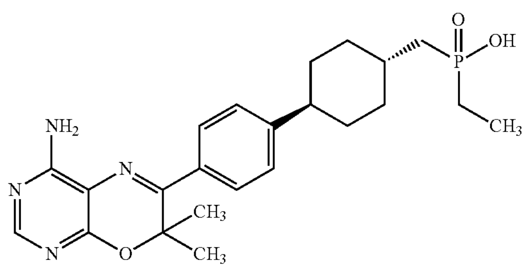 [SMILES: CCP(=O)(O)C[C@H]1CC[C@H](c2ccc(C3=Nc4c(N)ncnc4OC3(C)C)cc2)CC1] | C: 61.18, H: 7.14, N: 12.41<br>C: 61.33, H: 7.27, N: 12.26<br>$C_{23}H_{31}N_4O_3P + 0.5 H_2O$ | 444 |
| 23 | 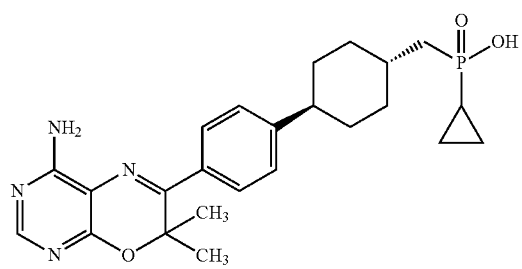 [SMILES: CC1(C)Oc2ncnc(N)c2N=C1c1ccc([C@H]2CC[C@H](CP(=O)(O)C3CC3)CC2)cc1] | C: 62.19, H: 6.96, N: 12.09<br>C: 62.17, H: 6.87, N: 11.91<br>$C_{24}H_{31}N_4O_3P + 0.5 H_2O$ | 455 |
| 24 | 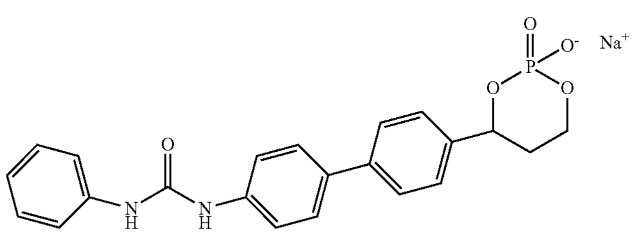 [SMILES: O=C(Nc1ccccc1)Nc1ccc(-c2ccc(C3CCOP(=O)([O-])O3)cc2)cc1 ; [Na+]] | | 425 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
|---|---|---|---|
| 25 | 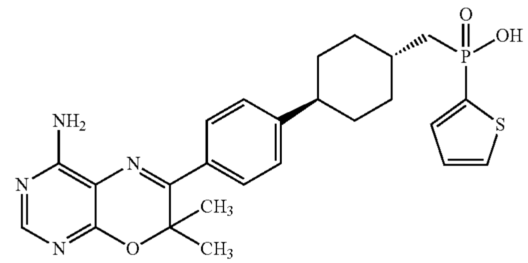 [SMILES: CC1(C)Oc2ncnc(N)c2N=C1c1ccc([C@H]2CC[C@H](CP(=O)(O)c3cccs3)CC2)cc1] | C: 58.35, H: 6.07, N: 10.89<br>C: 59.34, H: 6.06, N: 10.86<br>$C_{25}H_{29}N_4O_3PS + 1\ H_2O$ | 497 |
| 26 | 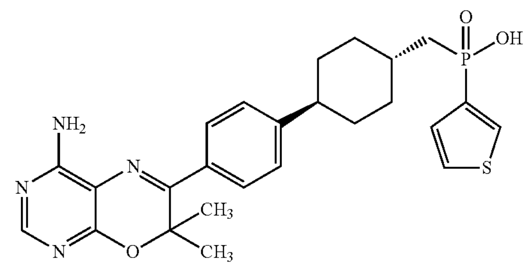 [SMILES: CC1(C)Oc2ncnc(N)c2N=C1c1ccc([C@H]2CC[C@H](CP(=O)(O)c3ccsc3)CC2)cc1] | C: 59.82, H: 5.94, N: 11.16<br>C: 60.04, H: 6.09, N: 10.94<br>$C_{25}H_{29}N_4O_3PS + 0.3\ H_2O$ | 497 |
| 27 | 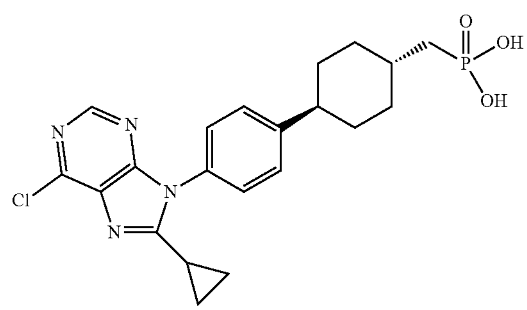 [SMILES: O=P(O)(O)C[C@H]1CC[C@H](c2ccc(-n3c(C4CC4)nc4c(Cl)ncnc43)cc2)CC1] | C: 54.05, H: 5.66, N: 12.01<br>C: 54.36, H: 5.75, N: 11.54<br>$C_{21}H_{24}ClN_4O_3P + 1.1\ H_2O$ | 447 |
| 28 | 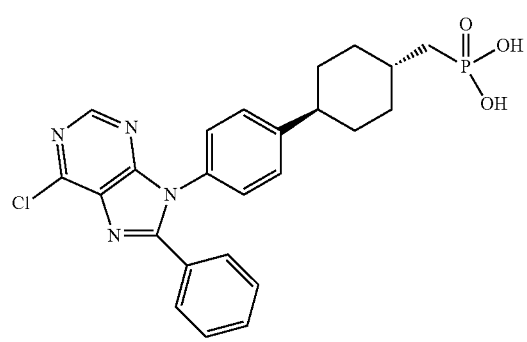 [SMILES: O=P(O)(O)C[C@H]1CC[C@H](c2ccc(-n3c(-c4ccccc4)nc4c(Cl)ncnc43)cc2)CC1] | C: 56.13, H: 5.38, N: 10.91<br>C: 56.39, H: 5.38, N: 10.30<br>$C_{24}H_{24}ClN_4O_3P + 1.7\ H_2O$ | 483 |
| 29 | 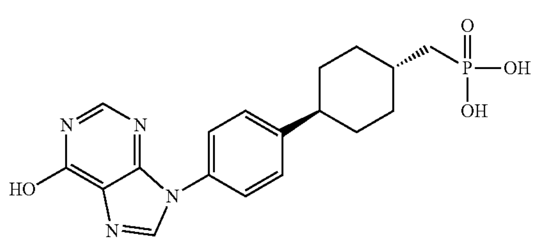 [SMILES: O=P(O)(O)C[C@H]1CC[C@H](c2ccc(-n3cnc4c(O)ncnc43)cc2)CC1] | C: 49.88, H: 6.05, N: 12.93<br>C: 49.67, H: 5.23, N: 12.82<br>$C_{18}H_{21}N_4O_4P + 2.5\ H_2O$ | 389 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
|---|---|---|---|
| 30 | (structure: 4-amino-pteridine-oxazine with dimethyl, phenyl-cyclohexyl-O-P(=O)(OH)-O-CH₂-pyridin-3-yl) | C: 57.67, H: 5.96, N: 12.93<br>C: 57.83, H: 5.80, N: 10.48<br>$C_{26}H_{30}N_5O_5P$ + 1.0 H₂O | 524 |
| 31 | (structure: 4-amino-pteridine-oxazine with dimethyl, phenyl-cyclohexyl-O-P(=O)(OH)-O-CH₂-pyridin-4-yl) | C: 59.65, H: 5.78, N: 13.38<br>C: 59.68, H: 5.81, N: 10.84<br>$C_{26}H_{30}N_5O_5P$ | 524 |
| 32 | (structure: 4-amino-pteridine-oxazine with dimethyl, phenyl-cyclohexyl-CH₂-P(=O)(OH)-butyl) | C: 61.92, H: 7.61, N: 11.55<br>C: 62.11, H: 8.15, N: 11.19<br>$C_{25}H_{35}N_4O_3P$ + 0.8 H₂O | 471 |
| 33 | (structure: 4-amino-pteridine-oxazine with dimethyl, phenyl-cyclohexyl-CH₂-P(=O)(OH)-isopropyl) | C: 59.84, H: 7.49, N: 11.63<br>C: 59.64, H: 7.88, N: 11.31<br>$C_{24}H_{33}N_4O_3P$ + 1.4 H₂O | 457 |
| 34 | (structure: 4-amino-pteridine-oxazine with dimethyl, phenyl-cyclohexyl-CH₂-P(=O)(OH)-(3-chlorophenyl)) | C: 60.22, H: 5.90, N: 10.40<br>C: 60.55, H: 6.30, N: 10.08<br>$C_{27}H_{30}ClN_4O_3P$ + 0.75 H₂O | 525 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
|---|---|---|---|
| 35 | 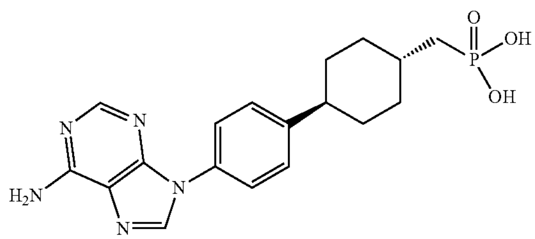 [SMILES: Nc1ncnc2c1ncn2-c1ccc([C@H]2CC[C@H](CP(=O)(O)O)CC2)cc1] | C: 54.30, H: 5.87, N: 17.59<br>C: 54.59, H: 5.71, N: 17.17<br>$C_{18}H_{22}N_5O_3P$ + 0.6 $H_2O$ | 388 |
| 36 | 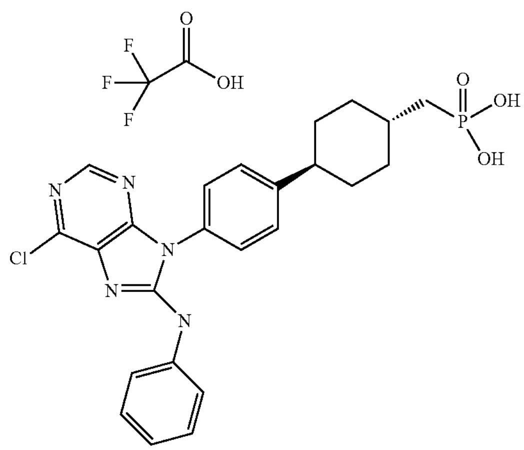 | C: 51.03, H: 4.28, N: 11.44<br>C: 51.33, H: 4.40, N: 11.67<br>$C_{24}H_{25}ClN_5O_3P$ + 1.0 $CF_3CO_2H$ | 498 |
| 37 | 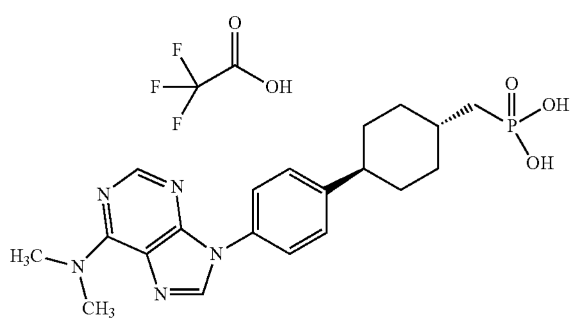 | C: 48.16, H: 4.88, N: 12.42<br>C: 48.37, H: 4.96, N: 12.77<br>$C_{20}H_{26}N_5O_3P$ + 1.3 $CF_3CO_2H$ | 416 |
| 38 | 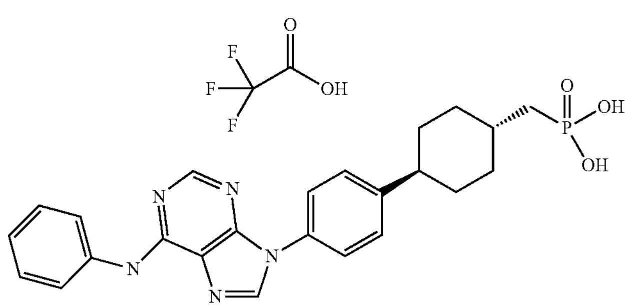 | C: 52.23, H: 4.50, N: 11.45<br>C: 52.16, H: 4.40, N: 11.57<br>$C_{24}H_{26}N_5O_3P$ + 1.3 $CF_3CO_2H$ | 464 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
|---|---|---|---|
| 39 | 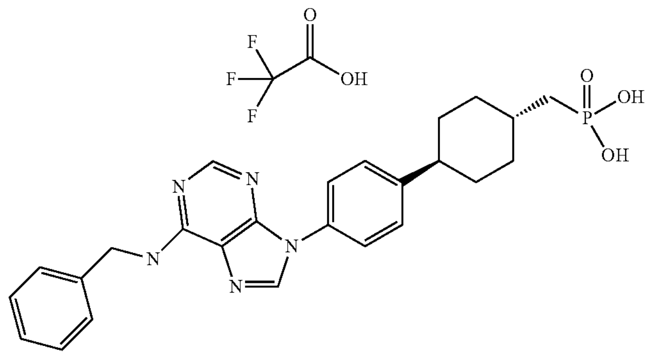 | | |
| 40 | 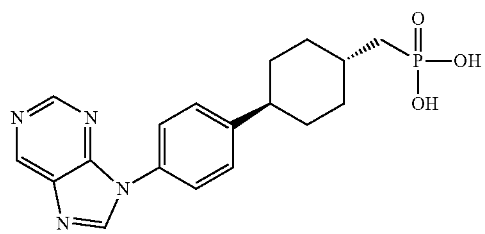 [SMILES: O=P(O)(O)C[C@H]1CC[C@H](c2ccc(-n3cnc4cncnc43)cc2)CC1] | C: 58.06, H: 5.68, N: 15.05<br>C: 57.83, H: 5.68, N: 14.97<br>$C_{18}H_{21}N_4O_3P$ | 373 |
| 41 | 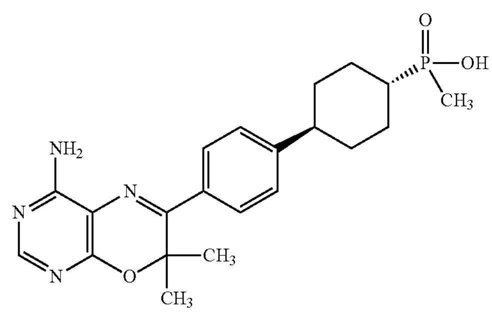 [SMILES: CC1(C)Oc2ncnc(N)c2N=C1c1ccc([C@H]2CC[C@H](P(C)(=O)O)CC2)cc1] | | 415 |
| 42 | 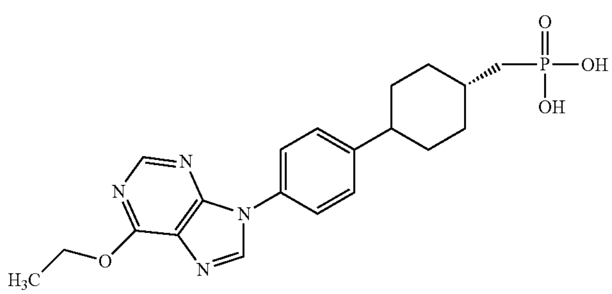 | | 417 |
| 43 | 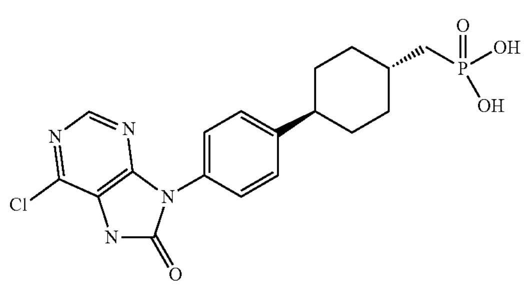 [SMILES: O=c1[nH]c2c(Cl)ncnc2n1-c1ccc([C@H]2CC[C@H](CP(=O)(O)O)CC2)cc1] | | 423 |

TABLE 1-continued

Elemental Analysis and Mass Spec Data of Certain Compounds of the Present Invention

| Compound Number | Structure | Elemental Analysis CHN (calcd) CHN (Found) Formula | Mass Spec MH+ |
|---|---|---|---|
| 44 | 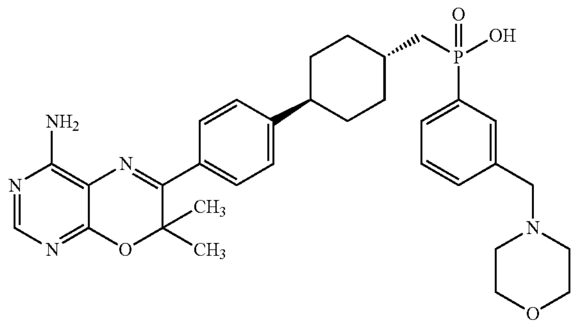 [SMILES: CC1(C)Oc2ncnc(N)c2N=C1c1ccc([C@H]2CC[C@H](CP(=O)(O)c3cccc(CN4CCOCC4)c3)CC2)cc1] | | 590 |
| 45 | 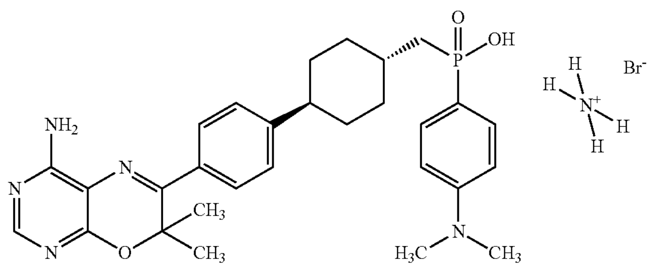 [SMILES: CN(C)c1ccc(P(=O)(O)C[C@H]2CC[C@H](c3ccc(C4=Nc5c(N)ncnc5OC4(C)C)cc3)CC2)cc1 ; [NH4+] ; [Br-]] | | 534 |
| 46 | 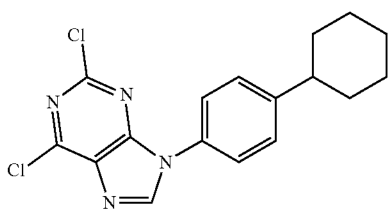 [SMILES: Clc1nc(Cl)c2ncn(-c3ccc(C4CCCCC4)cc3)c2n1] | | 384 |
| 47 | 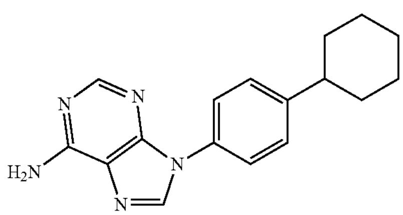 [SMILES: Nc1ncnc2c1ncn2-c1ccc(C2CCCCC2)cc1] | | 294 |
| 48 | 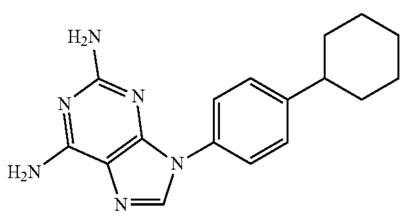 [SMILES: Nc1nc(N)c2ncn(-c3ccc(C4CCCCC4)cc3)c2n1] | | 309 |
| 49 | 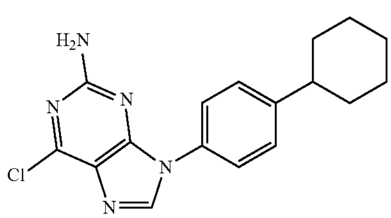 [SMILES: Nc1nc(Cl)c2ncn(-c3ccc(C4CCCCC4)cc3)c2n1] | | 328 |

TABLE 1-continued

Elemental Analysis and Mass Spec Data of Certain
Compounds of the Present Invention

| Compound Number | Structure | Elemental Analysis CHN (calcd) CHN (Found) Formula | Mass Spec MH+ |
|---|---|---|---|
| 50 | 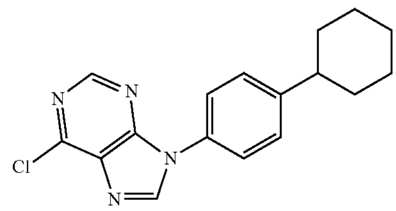 [SMILES: Clc1ncnc2c1ncn2-c1ccc(C2CCCCC2)cc1] | | 313 |
| 51 | 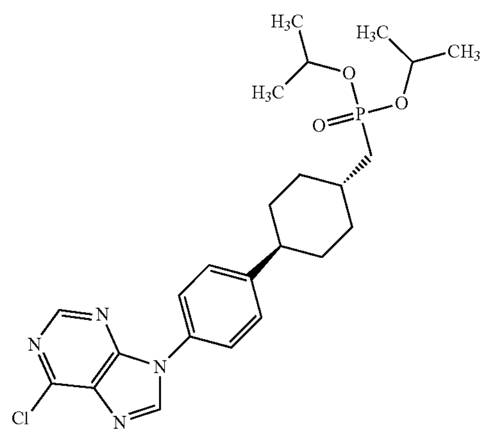 [SMILES: CC(C)OP(=O)(C[C@H]1CC[C@H](c2ccc(-n3cnc4c(Cl)ncnc43)cc2)CC1)OC(C)C] | | 491 |
| 52 | 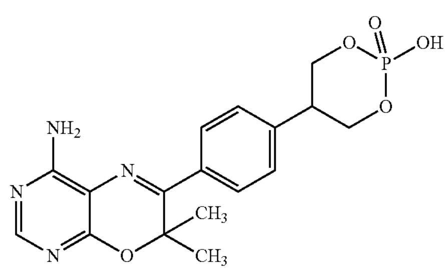 [SMILES: CC1(C)Oc2ncnc(N)c2N=C1c1ccc(C2COP(=O)(O)OC2)cc1] | | 390 |
| 53 | 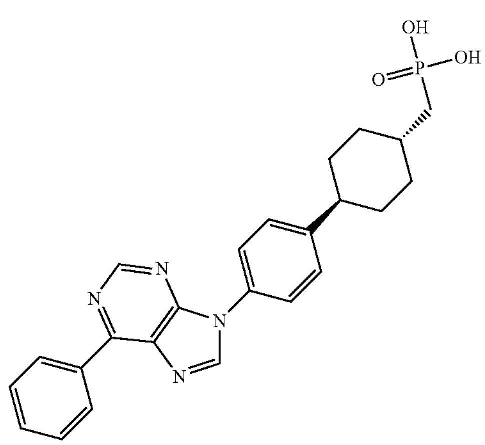 [SMILES: O=P(O)(O)C[C@H]1CC[C@H](c2ccc(-n3cnc4c(-c5ccccc5)ncnc43)cc2)CC1] | | 449 |

Preparation of Compounds

The synthesis of compounds of Formula (I), wherein the groups Q, $Q^1$, $Q^2$, $Q^3$, $Q^4$, $Q^5$, $Q^6$, $Q^7$, $Q^8$, $Q^9$, $G^1$, $G^2$, $G^3$, $G^4$, Z, $Z^1$, $Z^2$, X, $X^1$, $X^2$, T, E, J, A, D, T, $R^a$, $R^b$, $R^1$, $R^2$, $R^3$, $R^4$, $R^5$, $R^6$, $R^7$, $R^8$, $R^9$, $R^{10}$, $R^{11}$, $R^{12}$ and integers t, m, or n have the meanings as set forth in the Detailed Description section unless otherwise noted, is exemplified in Schemes 1-8.

Compounds of the present invention can be prepared beginning with commercially available starting materials and using general synthetic techniques known to those of skill in the art. Outlined below are reaction schemes suitable for preparing such compounds.

As illustrated in Scheme 1, compounds of formula 5 can be synthesized starting from commercially available compounds such as of formula 1. These carbonyl compounds upon Wittig type condensation with methylenediphosphonate ester in presence of a base result in the homologoted unsaturated phosphonate adducts (Xu et al, *J. Org. Chem.*, 1996, 61, 7697-7701). The resulting olefins undergo facile hydrogenation to give trans-1,4- or 1,3-substituted (depending on n variable of the starting materials of formula 1) compounds of formula 2. The conditions of such hydrogenations may be similar to the earlier reported protocols as in WO04047755. Preparation of compounds of formula 3 from 2 may be attained by selective preparation of monophosphonochloridate followed by reaction with aryl or heteroaryl or alkyl or cycloalkyl magnesium halides as previously reported (Morise et al, *J. Chem. Soc. Perkin Trans. I*, 1996, 2179-2185). Alternatively, H-phosphinates formed from compounds of formula 2 may be coupled to aryl or heteroaryl halide or triflate under palladium catalyzed reaction conditions to introduce -X2-W group as in formula 3 (Bennett et al, *J. Chem. Soc. Perkin Trans. I*, 1995, 1145-1151).

Synthesis of compounds of formula 4 from 3 can be attained as described earlier in WO04047755.

Deprotection of phosphorus ester of 4 can be achieved by a variety of methods depending on the choice of R' group. Alkyl esters undergo deprotection under bromotrimethyl silane (TMSBr) hydrolysis conditions. Hexamethyl disilazane is used as an additive with TMSBr where the substrate is acid-sensitive. Acid mediated deprotection conditions are used for t-butyl esters. In case of phenyl substituted esters, deprotection may be achieved by base hydrolysis. Whereas, benzyl or allyl esters undergo deprotection in neutral conditions such as hydrogenation in the presence of a catalyst and reaction by palladium catalysis, respectively. These deprotection conditions exemplified for conversion of 4 to 5 may be utilized across all the synthetic sequences that are described herein (Schemes 1-8).

Scheme 1

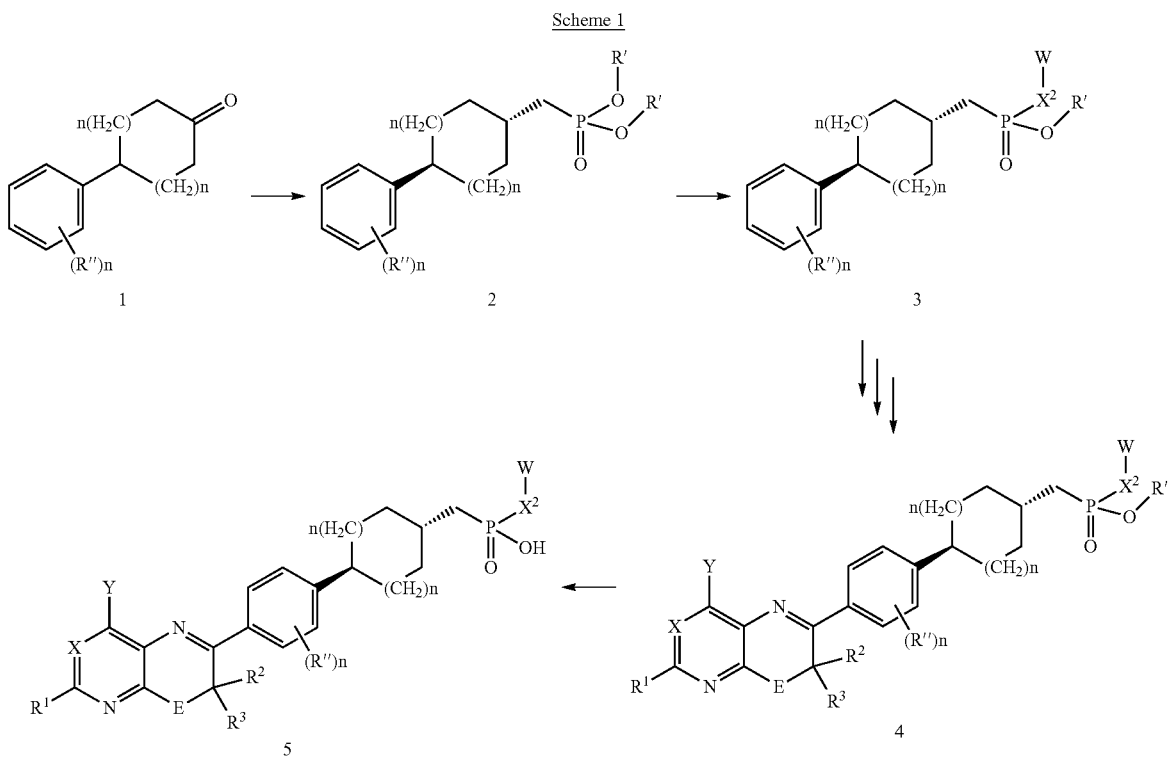

Alternatively, Z group substitution may be introduced at a later stage of the synthesis as shown in scheme 3. Such a synthetic strategy may be applied to prepare compounds of formula 11 from 10 where Q is substituted with $Q^1$, $Q^2$, $Q^3$, $Q^4$, $Q^5$, $Q^8$ or $Q^9$. Compounds of formula 10 can be attained following earlier described procedures in WO04047755, WO08067257, WO08134690, WO08134693, WO06064189, WO06134317, WO07071966, WO07138304, WO07138311, WO07141502, WO07141517, WO07141538, WO07141545, WO07144571, and WO08129319. Introduction of Z group substitution is accomplished by coupling of compounds of formula 7 with 10. Such coupling reactions where $X^1$ of 10 is O or S and leaving group (LG) of 7 is Cl or a substituted or non-substituted phenyl group can be achieved by magnesium alkoxides mediated reactions (WO07022073). Compounds of formula 7 may be synthesized by a nucleophilic displacement reaction of 8. In addition, compounds of Formula 7 can be prepared by applying other methods known in the art. For example, Pd-catalyzed reactions of aryl, heteroaryl or enol triflate (Kalek et al, *Org. Lett.,* 2008, 10, 4637-4640, Bonnaventure et al, *J. Org. Chem.* 2008, 73, 6330-6340) or base mediated reactions of benzylic type of halides with phosphinate 9 (Hubbard et al, *Bioorg. Med. Chem. Lett.,* 2008, 18, 679-681. Boyd et al, *Tetrahedron Lett.,* 1996, 37, 5425-5426; Ando et al, *J Org. Chem.,* 1999, 64, 8406-8408), or by a well-known Arbuzov type of reactions with 6 (Perumal et al, *J Org Chem.,* 2006, 71, 4778-4785).

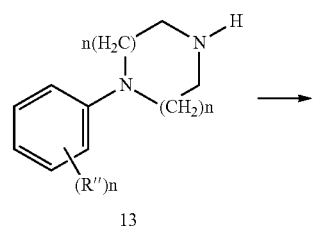

Scheme 2

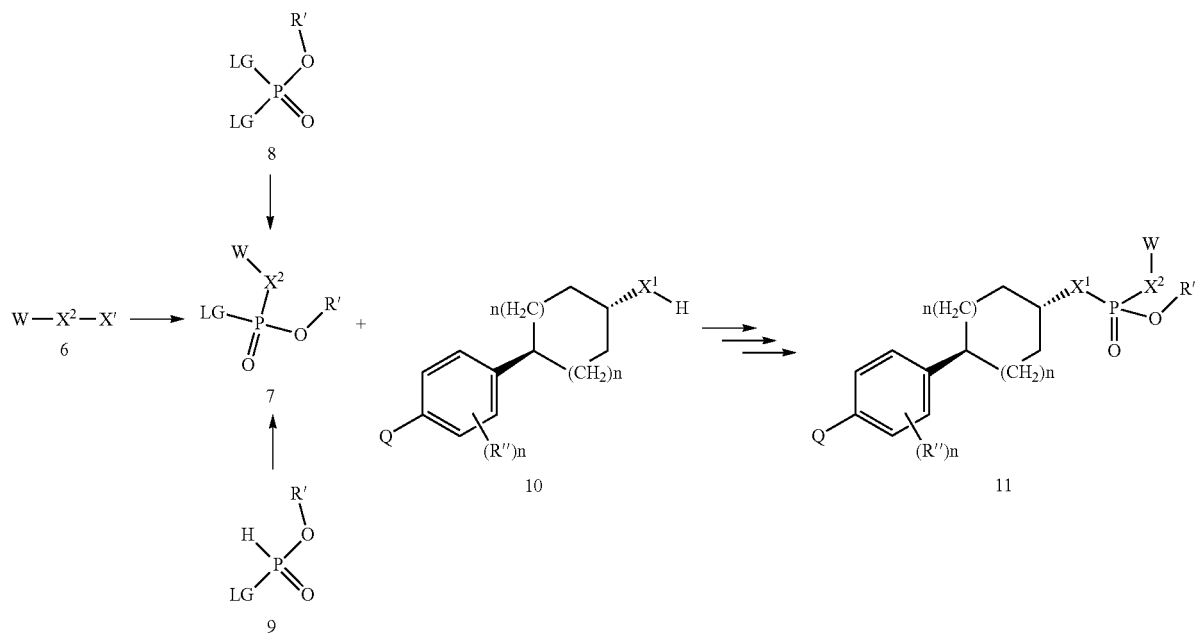

Compounds that have heterocyclic substitution as in 15 may be obtained from 13 via coupling of precursors of formula 12. Such sequence to 15 may be a linear synthesis as in scheme 1 or convergent sequence as in scheme 3. Synthesis of compounds of formula 12 can be achieved from commercially available halomethylene phosphonate diesters via the transformations that were described earlier in scheme 1, in the conversion of compounds of formula 2 to 3. Base mediated coupling of 12 and 13 to 14 and conversion to 15 may be achieved as described in WO04047755.

Scheme 3

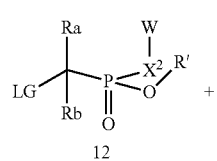

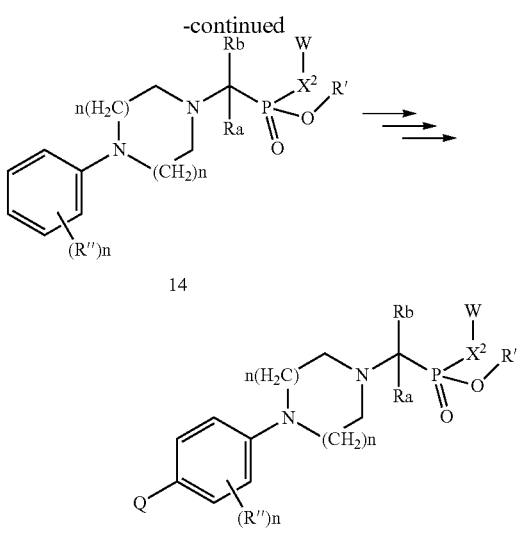

Compounds of formula 17 (Scheme 4) can be synthesized from 16 where X''' is —OH or —NH$_2$ as described in WO09016462. Compounds of 16 where X''' is —OH may be attained starting from a commercially available hydroxyl substituted 1 following the chemistry described in scheme 1. Compounds where X''' in 16 is —NH$_2$ are obtained by direct nitration and reduction sequence (WO07141502) from 2, or via 16 where X''' is substituted with —OH, by Pd mediated amination of corresponding triflate (WO07141517).

Scheme 4

2 ⟶

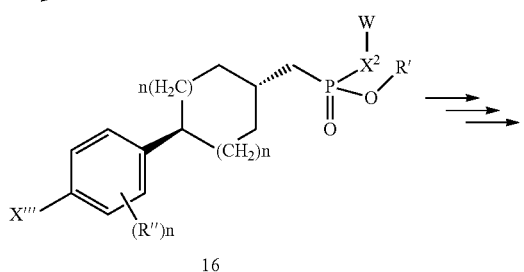

16

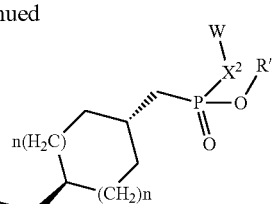

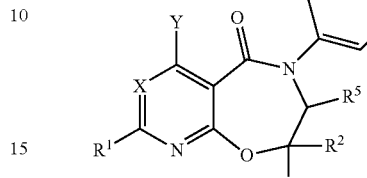

17

The methods described for amine precursor 16 may also be applied in the preparation of compounds of formula 19 with diverse G3 substitution. Such amines of 16 or 19 can be utilized in the synthesis of compounds of formulae of 20 to 22. Synthetic procedures described in WO05044250, WO06064189, WO06134317, WO07071966, WO07138304, WO07138311, WO07141502, WO07141517, WO07141538, WO07141545, WO07144571, WO08129319 may be utilized for the preparation of compounds of formulae of 20 to 22.

Scheme 5

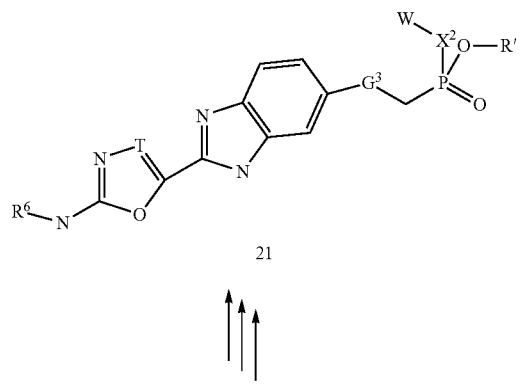

21

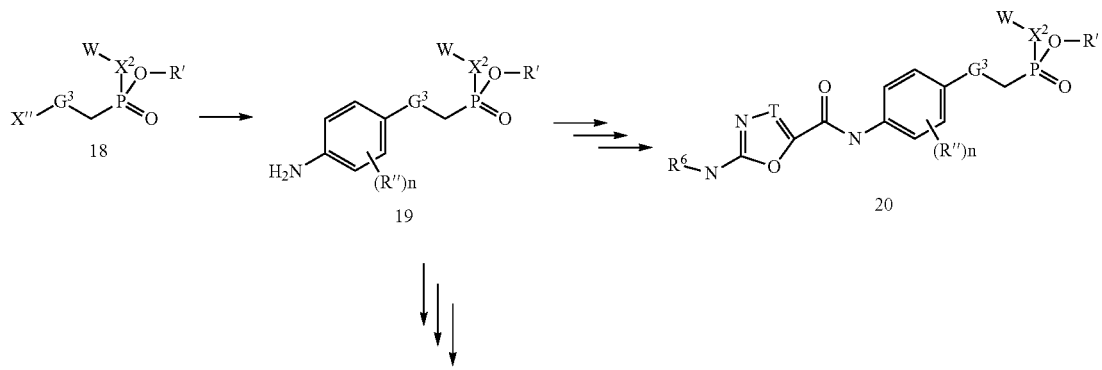

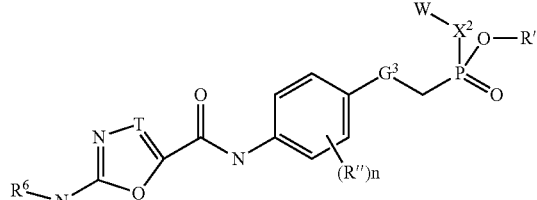

22

Compounds of formula 25 can be attained from 16 where X''' is —NH$_2$, via displacement reaction of a commercially available substituted pyrimidine, pyridine or a phenyl substituted precursor (23). Reduction of the resulting displacement product followed by cyclization with a desired R$^8$ substituted carboxylic acid or aldehyde result in the compounds of formula 25. Alternatively, compounds of 25 can be prepared via a copper mediated N-arylation reaction of 26 and an appropriately functionalized heterocycle as 27 (Jacobsen et al, *J. Org. Chem.* 2006, 71, 9183-9190).

Scheme 6

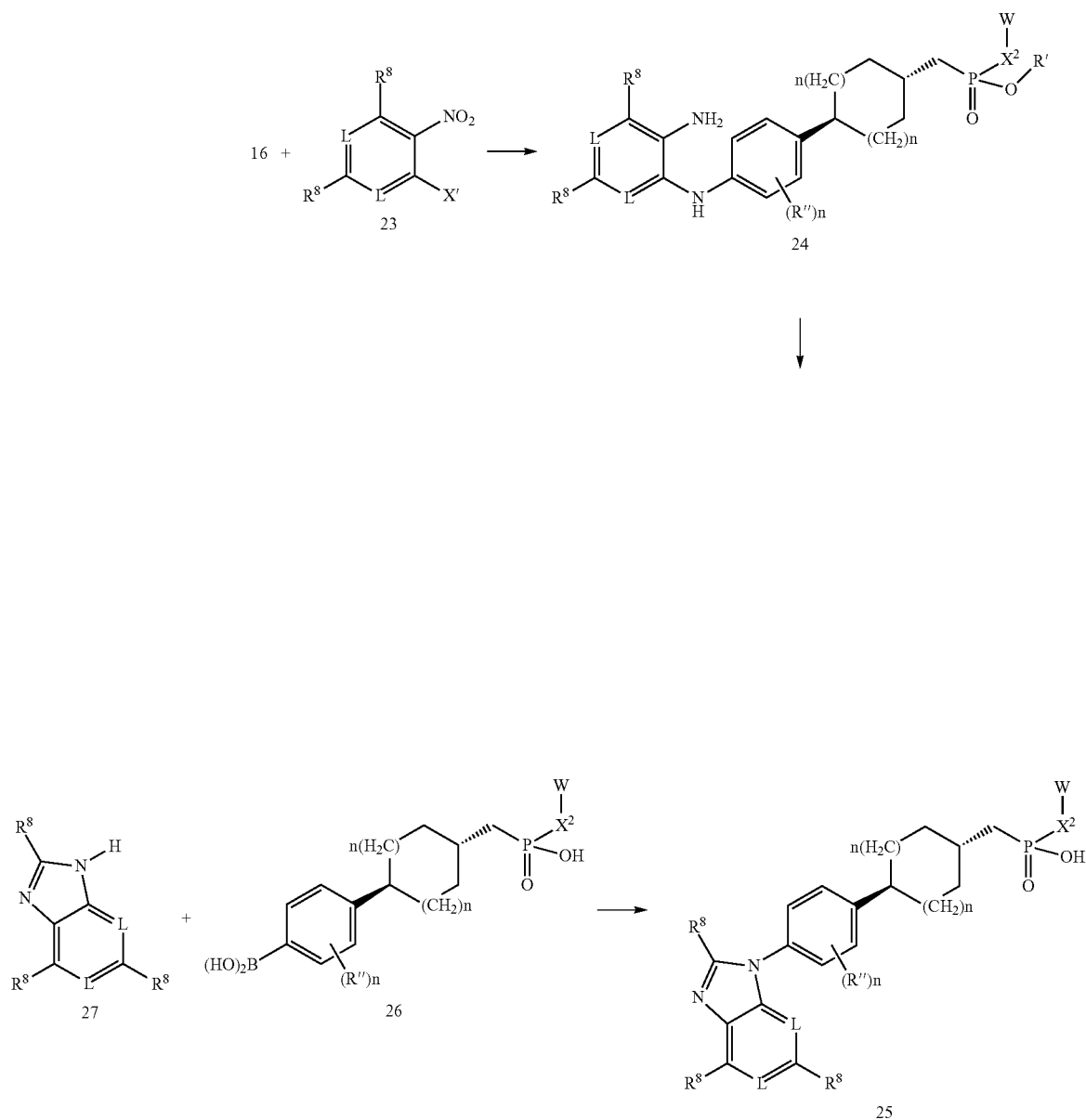

Compounds of formulae 31 and 32 can be made from 29 where X" is a group selected from Br, I or triflate, utilizing the earlier described procedures (WO07137103, WO07137107, WO06113919). Preparation of 29 from 28 or 30 from corresponding unsaturated esters may be obtained by Michael-type additions (Green, *Tetrahedron Lett.,* 1989, 30, 4807-4810). Intermediates of formula 30 may be transformed to 29 by Friedel-Crafts acylation reaction (Zhao et al, *J. Med. Chem.,* 2008, 51, 380-383).

Scheme 7

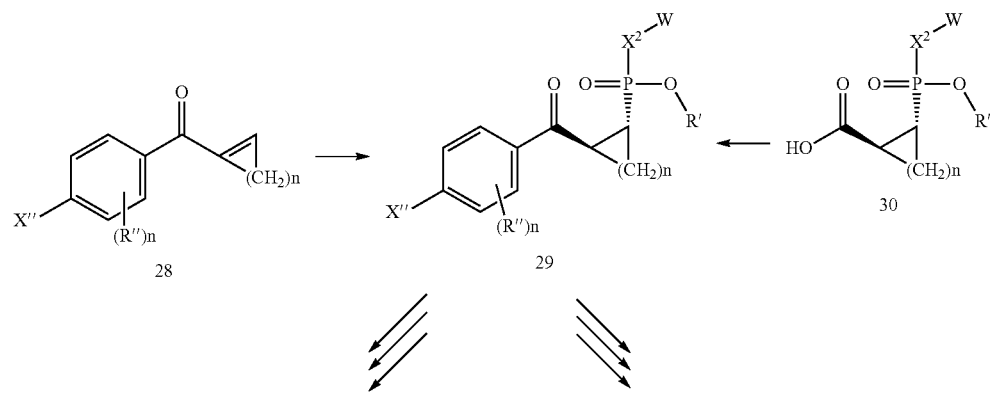

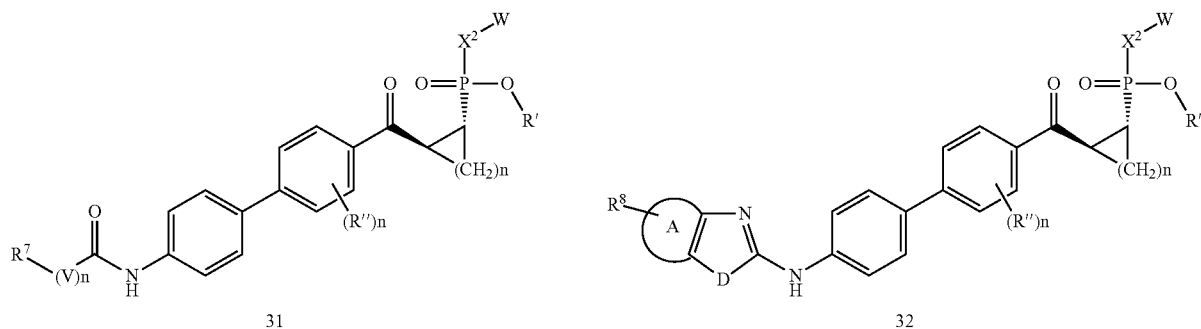

Preparation of compounds of 34 from intermediate 33 may be attained by utilizing the procedures described before (WO07137103, WO07137107, WO06044775, WO07016538, WO08099221, and WO09011285). Substituted amino phosphonic acid esters can be made with the procedures that are well-known in the literature (Chandrasekhar et al, Synlett, 2003, 4, 505-506). Monoester 33 can be prepared from corresponding diesters via the reactions described earlier, from 2 to 3. Such compounds can also be made in enatiomerically pure form when $R^{10}$ and $R^{11}$ are not equivalent (Ordonez et al, Tetrahedron, 2009, 65, 17-49).

Scheme 8

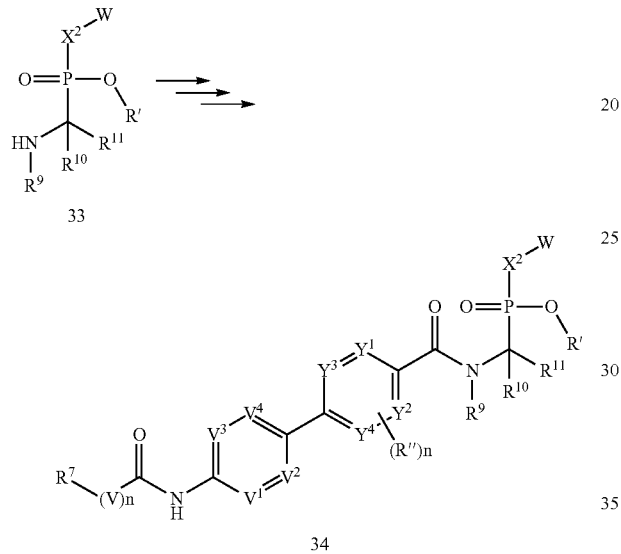

34

Methods of preparation of compounds of the present invention described in schemes 2 to 8 delineate the synthesis of phosphorus esters, protected with R' group. Such R' group may be selected from alkyl, allyl, aryl or benzyl substituents. These esters may be deprotected to compounds of Formula I in conditions described for compounds of formula 5 from 4 in scheme 1.

BIOLOGICAL EXAMPLES

Example A

Inhibition of Rat and Human Microsomal DGAT Activity

The inhibition of DGAT-1 activity can be assessed in intestinal microsome preparations by monitoring the incorporation of radiolabeled fatty acyl-CoA into DAG.

Methods: Commercial microsomal preparations containing 60 ug of protein are incubated in assay buffer [20 uM 1,2-didecanloyl glycerol, 5 uM $^{14}$C decanoyl-CoA, 5 mM $MgCl_2$, 0.4% BSA, 0.1% dimethyl sulfoxide (DMSO), 50 mM HEPES-pH 7.5] in the presence of varying concentrations of inhibitors that are dispensed from 100% DMSO stock solutions. Final assay volumes are 200 uL. Reactions are carried out for 45 minutes in 96-well polystyrene microtiter plates at ambient temperature. Following the ambient temperature incubation, assay mixtures are applied to a 96-well filter plate (Catalog # MSHVN4510, Millipore Inc.; Billerica, Mass.) under vacuum. The filter plate is pre-equilibrated with 100 uL of 70% ethanol followed by 200 uL of assay buffer. Filters are dried, removed and placed in scintillation vials with 4 mL of scintillation cocktail (Catalog #6013329; PerkinElmer Inc.; Waltham, Mass.). De novo $^{14}$C-TAG formed in the assay and trapped on the filters is quantified with use of a liquid scintillation counter (Model # LS6500 Beckman Coulter, Inc.; Fullerton, Calif.). The $IC_{50}$ is defined as the concentration of compound that results in a 50% reduction in TAG synthesis.

Results:

TABLE 2

DGAT-1 Inhibition of Compounds of the Present Invention

| Compound Number | hDGAT1 $IC_{50}$* |
|---|---|
| 1 | A |
| 2 | B |
| 3 | A |
| 5 | A |
| 6 | C |
| 7 | C |
| 8 | A |
| 9 | A |
| 10 | A |
| 11 | A |
| 12 | B |
| 13 | A |
| 14 | A |
| 17 | A |
| 18 | B |
| 19 | A |
| 20 | A |
| 21 | A |
| 22 | B |
| 23 | A |
| 24 | C |
| 25 | B |
| 26 | B |
| 30 | B |
| 31 | B |
| 32 | B |
| 33 | B |
| 34 | B |

*'A' represents $IC_{50}$ value < 10 nM
'B' represents $IC_{50}$ value between 10 and 100 nM
'C' represents $IC_{50}$ value between 100 and 1000 nM Example B In Vivo Assay for Intestinal Triglyceride Export The following screen can be used to evaluate the effects of DGAT-1 inhibitors on the export of dietary TAGs from the intestine to the circulation in rodents (male Sprague Dawley rats or C57BL/6 mice).

Methods: Animals (housed 2/cage) are fasted overnight, and dosed (PO) the next day with vehicle (1% Tween-80) or test compound at doses ranging from 0.01 to 30 mg/kg, followed by an oral gavage of olive oil. Blood samples are taken at baseline and at appropriate intervals over the course of 4 hours. Serum TAG levels are determined using the Infinity triglyceride reagent per the manufacturer's instructions.

Results: Compounds 1, 2, and 5 reduced the $AUC_{0-4h}$ of serum TAGs following oral administration to Sprague Dawley rats at doses in the range of 0.1 to 30 mg/kg. These results confirm inhibition of enterocyte DGAT-1 by the compounds tested.

Example C

Determination of Plasma Pharmacokinetics and Oral Bioavailability in Rats

Pharmacokinetic studies in rats are useful for the identification of DGAT-1 inhibitors that have low oral bioavailability and show low systemic exposure (i.e. low circulating levels in plasma).

Methods: Groups of male Sprague Dawley rats (200-250 g) (n=3/group) were administered either an IV bolus (1% Tween-80, pH adjusted to 7, vehicle) or an oral gavage (50% PEG-200 in 1% Tween-80 vehicle) of 5 mg/kg of each DGAT-1 inhibitor. Blood (EDTA) was collected by tail nick at 0.5, 1, 2, 4, 8, 10-12 and 24 hr post dose. Following centrifugation of the blood to obtain plasma, the samples were analyzed by LC-MS/MS method for active metabolite. The pharmacokinetic parameters were calculated by non-compartmental analysis of the plasma concentration-time profile of the active metabolite. The oral bioavailability was determined by dividing the dose-normalized plasma AUC value of the active metabolite following oral administration of the DGAT-1 inhibitor by the plasma AUC value of the active metabolite after IV bolus administration.

Results: A summary of the key plasma pharmacokinetic parameters of the DGAT-1 inhibitors evaluated is shown in the table below. Compounds of the invention that were tested have low oral bioavailability, <10%, and low systemic exposure as indicated by a Cmax<0.01 ug/mL. In contrast, known DGAT inhibitors X, Y, and Z were found to have high oral bioavailability and high plasma exposure.

TABLE 3

Key Plasma Pharmacokinetic Parameters of DGAT-1 Inhibitors[1,2]

| Compound | Oral bioavailability, % | Cmax, ug/mL |
|---|---|---|
| X | 75 | 4.81 |
| Y | 70 | 3.33 |
| Z | 67 | 8.68 |
| 1 |  5.6 | 0.009 |
| 2 |  1.1 | 0.005 |
| 5 |  0.9 | 0.003 |

[1]LOQ = 0.001 ug/mL
[2]Compound X, Compound 2 of Birch et al, J. Med. Chem., 2009 (DOI: 10.1021/jm801507v); Compound Y, compound 1 of Birch et al, J. Med. Chem., 2009 (DOI: 10.1021/jm801507v); Compound Z, Example 1 of WO07144571.

Example D

In Vivo Assay for Effects on Food Intake

The following assay can be used to evaluate the anorectic efficacy of DGAT-1 inhibitors rodents (male Sprague Dawley rats or C57BL/6 mice).

Methods: Animals (rats housed 1/cage, or mice housed 2/cage) are fasted overnight. The next morning, animals are dosed (PO) with vehicle (1% Tween-80) or test compound (doses ranging from 0.1 to 30 mg/kg). Food is then presented immediately following vehicle or compound administration. Food is weighed manually at 1-3 hour intervals to determine any inhibitory effects on food intake.

Results: Compounds of the invention reduced food intake significantly following oral administration at doses ranging from 0.1 to 30 mg/kg.

Example E

In Vivo Assay for Gut Hormone Secretion

The following procedure may be used to evaluate the effect of test compounds on gut hormone (e.g., PYY, GLP1, CCK, etc) secretion in rodents.

Methods: Animals (male Sprague Dawley rats or C57BL/6 mice) in a fed or fasted state are orally gavaged with a nutrient load (oil, carbohydrate, and/or protein) immediately following administration of vehicle or test compound (doses ranging from 0.01-30 mg/kg). Baseline and temporal bleeds are taken to determine serum concentrations of gut hormones of interest using commercially available ELISA/RIA kits as per the manufacturer's instructions.

Results: Administration of compounds of the invention to rodents at doses ranging from 0.1 to 30 mg/kg results in an increase in one or more gut hormones in plasma.

Example F

In Vivo Assay for Weight Loss and Reduction in Adiposity

The effects of DGAT-1 inhibitors on body weight and adiposity can be assessed in standard animal models of obesity such as the high-fat fed mouse or rat.

Methods: Mice (diet-induced obese male, C57BL/6) that have been fed a high fat diet for >12 weeks are sham-dosed bid with water until acclimated to dosing (as determined by stable or steadily increasing body weights). Thereafter, vehicle (1% Tween-80) or test compound (doses ranging from 0.3-30 mg/kg) are dosed (PO, bid) daily for up to 28 days. Food intake and body weights are monitored daily to determine anorectic and weight loss efficacy. At the end of the study, lean and fat mass can be assessed by NMR.

Results: Compounds of the invention significantly reduce body weight and adiposity after daily administration at doses ranging from 0.1 to 30 mg/kg for several days to several weeks.

Example G

In Vivo Assay for Determination of Insulin Sensitivity

The insulin tolerance test was developed to evaluate insulin sensitivity in humans and in animal models (Monzillo et al, Nutrition Reviews, 2003, 61(12):397-412; Bonora et al, J Clin Endocrinol Metab. 1989, 68:374-378; Bergman, Endocrine Reviews, 1985, 6:45-86). Diet-induced obese (DIO) mouse or rat models can become insulin resistant with prolonged high fat feeding and have been used to test for improved insulin sensitivity with insulin sensitizing drugs such as glitazones (Guerre-Millo M et al, JBC 2000 275: 16638-42; Schupp M et al; Diabetes, 2005 54: 3442-52; Arulmozhi DK, 2008, 60(9):1167-73) and in genetically manipulated mice (Fujii N. et al, Diabetes, 2008, 57:2958-66; Funato H et al, Cell Metabolism, 2009, 9(1): 64-76).

Methods: DIO mice or rats that were subchronically or acutely treated with vehicle or test compound (doses ranging from 0.1-30 mg/kg) are fasted for up to 14 hours and are injected (i.p., 1 U/kg) with Humalog (a fast-acting insulin analog). The temporal profile of blood glucose levels is monitored using One-Touch glucometers for up to 3 hours post-injection.

Results: Compounds of the invention improve insulin sensitivity after one or multiple weeks of dosing when administered at doses ranging from 0.1 to 30 mg/kg/day to DIO mice or rats. This is evident from the lower glucose levels following insulin administration in the treated versus the control animals.

REFERENCES

Chen, H. C., Stone, S. J., Zhou, P., Buhman, K. K., Farese, R. V. Jr. (2002) "Dissociation of obesity and impaired glucose disposal in mice overexpressing acyl coenzyme a:diacylglycerol acyltransferase 1 in white adipose tissue" *Diabetes* 51(11):3189-95.

Chen, H. C., Farese, R. V. Jr. (2005) "Inhibition of triglyceride synthesis as a treatment strategy for obesity: lessons from DGAT1-deficient mice" *Arterioscler Thromb Vasc Biol* 25(3):482-6.

Hill, J. O., Melanson, E. L., Wyatt, H. T. (2000) "Dietary fat intake and regulation of energy balance: implications for obesity" *J Nutr.* 30 (2S Suppl):284S-288S.

Shi, Y., Burn, P. (2004) "Lipid metabolic enzymes: emerging drug targets for the treatment of obesity" *Nat Rev Drug Discov* 3 (8):695-710.

Smith, S. J., Cases, S., Jensen, D. R., Chen, H. C., Sande, E., Tow, B., Sanan, D. A., Raber, J., Eckel, R. H., Farese, R. V. Jr. (2000) "Obesity resistance and multiple mechanisms of triglyceride synthesis in mice lacking Dgat" *Nat Genet* 25(1):87-90.

Stone, S. J., Myers, H. M., Watkins, S. M., Brown, B. E., Feingold, K. R., Elias, P. M., Farese, R. V. Jr (2004) "Lipopenia and skin barrier abnormalities in DGAT2-deficient mice" *J Biol Chem.* 19; 279(12): 11767-76.

Van Herpen, N. A., Schrauwen-Hinderling, V. B. (2008) "Lipid accumulation in non-adipose tissue and lipotoxicity" *Physiol Behav* 94(2):231-41.

Yamazaki, T., Sasaki, E., Kakinuma, C., Yano, T., Miura, S., Ezaki, O. (2005) "Increased very low density lipoprotein secretion and gonadal fat mass in mice overexpressing liver DGAT1" *J Biol Chem.* 280(22):21506-14.

Yen, C. L., Monetti, M., Burri, B. J., Farese, R. V. Jr. (2005) "The triacylglycerol synthesis enzyme DGAT1 also catalyzes the synthesis of diacylglycerols, waxes, and retinyl esters" *J Lipid Res* 46(7):1502-11.

Yen, C. L., Stone, S. J., Koliwad, S., Harris, C., Farese, R. V. Jr. (2008) "Thematic review series: glycerolipids. DGAT enzymes and triacylglycerol biosynthesis" *J Lipid Res* 49(11):2283-301.

Zhao, G., Souers, A. J., Voorbach, M., Falls, H. D., Droz, B., Brodjian, S., Lau, Y. Y., Iyengar, R. R., Gao, J., Judd, A. S., Wagaw, S. H., Ravn, M. M., Engstrom, K. M., Lynch, J. K., Mulhern, M. M., Freeman, J., Dayton, B. D., Wang, X., Grihalde, N., Fry, D., Beno, D. W., Marsh, K. C., Su, Z., Diaz, G. J., Collins, C. A., Sham, H., Reilly, R. M., Brune, M. E., Kym, P. R. (2008) "Validation of diacyl glycerolacyltransferase I as a novel target for the treatment of obesity and dyslipidemia using a potent and selective small molecule inhibitor" *J Med Chem* 51(3): 380-3.

We claim:
1. A compound of Formula (I), pharmaceutically acceptable salts or stereoisomers thereof,

$$Q\text{-}G^1\text{-}G^2\text{-}G^3\text{-}G^4\text{-}Z \qquad \text{Formula (I)}$$

wherein Q is

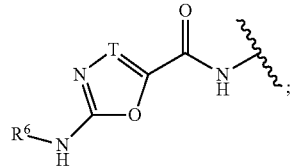

wherein $R^6$ is an optionally substituted aryl or optionally substituted heteroaryl group, wherein the optional substituents are one or more groups selected from a group H, $(C_1\text{-}C_4)$alkyl, halo, halo$(C_1\text{-}C_4)$alkyl, cyano, $(C_1\text{-}C_4)$alkoxy, $(C_1\text{-}C_4)$haloalkoxy, —C(O)$_x$R$^a$, —OR$^a$ —S(O)$_x$R$^a$, —NR$^a$R$^b$, —C(O)NR$^a$R$^b$, —NR$^a$C(O)R$^b$, —NR$^a$CO NR$^a$R$^b$, —S(O)$_2$ NR$^a$R$^b$ or —NR$^a$S(O)$_2$ NR$^a$R$^b$ where x is an integer of 1 or 2; and
T is N, CH or CMe;
$G^1$ and $G^3$ are independently selected from the group consisting of cyclo$(C_3\text{-}C_8)$alkylene, heterocyclo$(C_3\text{-}C_8)$alkylene, arylene and heteroarylene, optionally substituted with one or two groups independently selected from halo, $(C_1\text{-}C_6)$alkyl, $(C_2\text{-}C_6)$alkenyl, $(C_1\text{-}C_6)$alkoxy, cyano, $(C_1\text{-}C_6)$haloalkyl, $(C_1\text{-}C_6)$haloalkoxy, $(C_1\text{-}C_4)$perfluoroalkyl; —N(R$^a$ R$^b$), —N(R$^a$)—C(O)(R$^a$), —C(O)N(R$^a$)$_2$, —S(O)$_2$N(R$^a$)$_2$, —S(O)$_2$(R$^b$), —C(O)(R$^a$), wherein R$^a$ and R$^b$ are independently selected from the group consisting of H, $(C_1\text{-}C_8)$alkyl, $(C_2\text{-}C_8)$alkenyl, $(C_2\text{-}C_8)$alkynyl, fluoro$(C_1\text{-}C_8)$alkyl, $(C_3\text{-}C_8)$cycloalkyl, aryl, heteroaryl and aryl$(C_1\text{-}C_4)$alkyl;
$G^2$ is selected from the group consisting of a bond, $(C_1\text{-}C_4)$alkylene, $(C_2\text{-}C_4)$alkenylene, O, N(R$^a$)C(O), S and S(O)$_2$, wherein R$^a$ is selected from the group consisting of H, $(C_1\text{-}C_8)$alkyl, $(C_2\text{-}C_8)$alkenyl, $(C_2\text{-}C_8)$alkynyl, fluoro$(C_1\text{-}C_8)$alkyl, $(C_3\text{-}C_8)$cycloalkyl, aryl, heteroaryl and aryl$(C_1\text{-}C_4)$alkyl;
$G^4$ is X—Y—;
wherein X is selected from null, O, NH, CO, CHOH, S or S(O)$_2$; and Y is selected from $(C_1\text{-}C_4)$alkylene, $C_3\text{-}C_8$-cycloalkylene or heterocycloalkylene, —CH(R$^9$)C(R$^{10}$R$^{11}$)— or —N(R$^9$)C(R$^{10}$R$^{11}$)—;
wherein:
$R^{10}$ and $R^{11}$ are both hydrogen, and $R^9$ is hydrogen, $(C_1\text{-}C_6)$alkyl, $(C_1\text{-}C_6)$alkoxy, $(C_2\text{-}C_6)$alkenyl, phenoxy-$(C_2\text{-}C_6)$alkyl, 1-methyl-1H-indol-3-yl, bis[$(C_1\text{-}C_6)$alkyl]amino-$(C_2\text{-}C_6)$alkyl, 1-piperidinyl-$(C_2\text{-}C_6)$alkyl, 1-pyrrolidinyl-$(C_2\text{-}C_6)$alkyl, or 1-morpholinyl-$(C_2\text{-}C_6)$ alkyl; or $R^{10}$ and $R^{11}$ are both hydrogen and $R^9$ is $R^{12}(CH_2)_m$, where m is 0 to 3, and $R^{12}$ is phenyl optionally substituted with one or more halogen, hydroxy, $(C_1\text{-}C_6)$alkyl, $(C_1\text{-}C_6)$alkoxy, trifluoromethyl or cyano; or
$R^{10}$ and $R^{11}$ are both hydrogen and $R^9$ is $R^{12}(CH_2)_m$, where m is 0 to 3, and $R^{12}$ is 2-pyridinyl, 3-pyridinyl, or 4-pyridinyl, each of which is optionally substituted with halogen, $(C_1\text{-}C_6)$alkyl, $(C_1\text{-}C_6)$alkoxy, trifluoromethyl or cyano; or
$R^9$ is hydrogen, and $R^{10}$ and $R^{11}$ together with the carbon atom to which they are attached, form a three to five-membered ring, with 0 to 2 heteroatoms independently selected from O, S or N; or $R^{10}$ is hydrogen, and $R^9$ and $R^{11}$ together with the two carbon atoms to which they are attached, form a three- to six-membered ring with 0 to 2 heteroatoms independently selected from O, S or N;

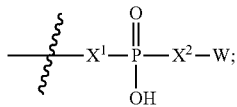

Z is $X^1$ and $X^2$ are independently selected from null, $(C(R^aR^b))_n$, O, $NR^a$, S or CO and n is 0 or 1; W is selected from H, $(C_1$-$C_6)$alkyl, aryl, heteroaryl or $(C_3$-$C_8)$cycloalkyl; wherein each of the $(C_1$-$C_6)$alkyl, aryl, heteroaryl and cycloalkyl is independently substituted with 1, 2, 3, 4, or 5 substituents independently selected from the group consisting of $(C_1$-$C_8)$alkyl, $(C_2$-$C_8)$alkenyl, $(C_2$-$C_8)$alkynyl, —CN, halogen, ethylenedioxy, methylenedioxy, haloalkyl, —$OR^a$, —O—C(O) ($R^a$), —$S(R^a)$, —$S(O)(R^b)$, —$S(O)_2(R^b)$, —$C(O)(R^a)$, —$C(O)(OR^a)$, —$N(R^a)_2$, —$N(R^a)$—$C(O)(R^a)$, —$C(O)N(R^a)_2$, —$S(O)_2N(R^a)_2$, —$(CR^aR^b)_tOR^a$, —$(CR^aR^b)_t$—O—$C(O)(R^a)$, —$(CR^aR^b)_tS(R^a)$, —$(CR^aR^b)_tS(O)(R^b)$, —$(CR^aR^b)_tS(O)_2(R^b)$, —$(CR^aR^a)_tC(O)(R^a)$, —$(CR^aR^b)_tC(O)(OR^a)$, —$(CR^aR^b)_tN(R^a R^b)$ —$(CR^aR^b)_tN(R^a)$—$C(O)(R^a)$, —$(CR^aR^b)_tC(O)N(R^a)_2$, —$(CR^aR^a)_tS(O)_2N(R^a)_2$ and —$(CR^aR^b)_tR^a$, —$(CR^aR^b)_tP(O)(OH)_2$, and —$(CR^aR^b)_tP(O)(OH)(R^a)$, wherein t is an integer of 1, 2, 3, or 4 and $R^a$ and $R^b$ are independently selected from the group consisting of H, $(C_1$-$C_8)$alkyl, $(C_2$-$C_8)$alkenyl, $(C_2$-$C_8)$alkynyl, fluoro $(C_1$-$C_8)$alkyl, $(C_3$-$C_8)$cycloalkyl, aryl, heteroaryl and aryl$(C_1$-$C_4)$alkyl; $X^1$ and $X^2$ may be combined to form a 5-, 6- or 7-membered ring having from 0 to 3 heteroatoms selected from the group consisting of $NR^a$, O and S; or $X^1$ or $X^2$ may be combined with W to form a 5-, 6-or 7-membered fused ring having from 0 to 3 heteroatoms selected from the group consisting of $NR^a$, O and S; and with a proviso that when $X^2$ is O, then $X^1$ is not $(C(R^aR^b))_n$.

2. The compound according to claim 1, wherein said compound is:

| Compound Number | Structure |
|---|---|
| 5 | 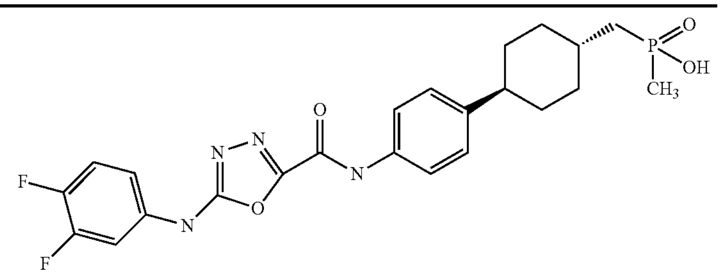 |

3. A pharmaceutically acceptable composition comprising a pharmaceutically acceptable carrier, vehicle or diluent and a compound according to claim 1.

4. The composition according to claim 3, wherein said compound is:

| Compound Number | Structure |
|---|---|
| 5 | 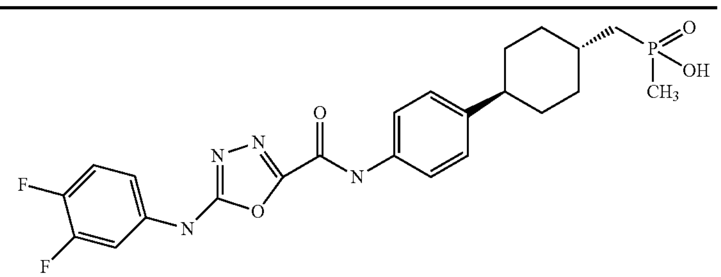 |

* * * * *

UNITED STATES PATENT AND TRADEMARK OFFICE
CERTIFICATE OF CORRECTION

PATENT NO. : 10,034,891 B2
APPLICATION NO. : 15/151740
DATED : July 31, 2018
INVENTOR(S) : K. Raja Reddy It is certified that error appears in the above-identified patent and that said Letters Patent is hereby corrected as shown below:

On the Title Page

Column 2, Item (57), Abstract, Line 6, change "hyperlipidiemias" to --hyperlipidemias--

On Page 2, Column 2, Item (56), Line 16, Other Publications, change "chioroalkylyphosphinates" to --chloroalkylphosphinates"--

On Page 2, Column 2, Item (56), Line 54, Other Publications, change "Triethyiphosphite;" to --Triethylphosphite;--

In the Specification

In Column 1, Line 33, change "CB 1" to --CB1--

In Column 6, Line 31, change "terms" to --term--

In Column 7, Line 26, change "terphthalic" to --terephthalic--

In Column 9, Line 34, change "—NR$^a$CO NR$^a$R$^b$," to -- —NR$^a$CONR$^a$R$^b$,--

In Column 9, Line 47, change "—(CR$^a$R$^b$)$_r$N(R$^a$ R$^b$)" to -- —(CR$^a$R$^b$)$_r$N(R$^a$R$^b$),--

In Column 9, Lines 53-61 (Approx.), change " 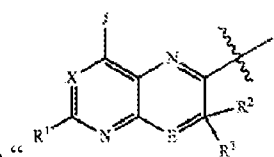 " to -- 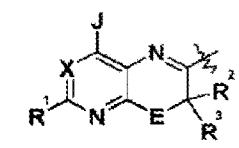 --

Signed and Sealed this
Twenty-seventh Day of November, 2018

Andrei Iancu
*Director of the United States Patent and Trademark Office*

CERTIFICATE OF CORRECTION (continued)

In Column 10, Lines 34-41 (Approx.), change " 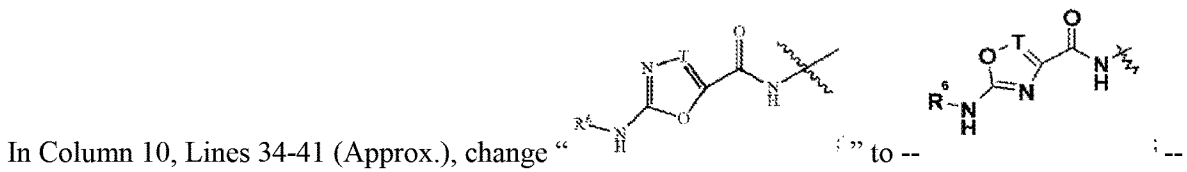 " to -- --

In Column 11, Line 1, change "—(CRᵃRᵇ)ᵣN(Rᵃ Rᵇ)" to -- —(CRᵃRᵇ)ᵣN(RᵃRᵇ),--

In Column 11, Line 44, change "bicylic" to --bicyclic--

In Column 11, Lines 53-54, change "—S(O)₂N(Rᵃ)₂" to -- —S(O)₂N(Rᵃ)₂,--

In Column 12, Line 42, change "—(CRᵃRᵇ)ₜS(O) (Rᵇ)," to -- —(CRᵃRᵇ)ₜS(O)(Rᵇ),--

In Column 13, Line 20, change "strearyl" to --stearyl--

In Column 16, Line 46, change "rosigliazone, pioglitozone" to --rosiglitazone, pioglitazone--

In Column 16, Line 47, change "asarabose;" to --acarbose;--

In Column 16, Line 51 (Approx.), change "taspoglatide;" to --taspoglutide;--

In Column 16, Line 52 (Approx.), change "sitaliptin;" to --sitagliptin;--

In Columns 17-18 (TABLE 1), Line 7, change "492" to --429--

In Columns 23-24 (TABLE 1-continued), Line 13 (Approx.), change "C: 55.65," to --C: 55.66,--

In Columns 25-26 (TABLE 1-continued), Line 14 (Approx.), change "11.08" to --N: 11.08--

In Columns 35-36 (TABLE 1-continued), Line 6 (Approx.), below "MH+" insert --478--

In Columns 37-38 (TABLE 1-continued), Line 9 (Approx.), change "384" to --348--

In Column 41, Line 50, change "homologoted" to --homologated--

In Columns 47-48, Lines 1-9 (Approx.), change " 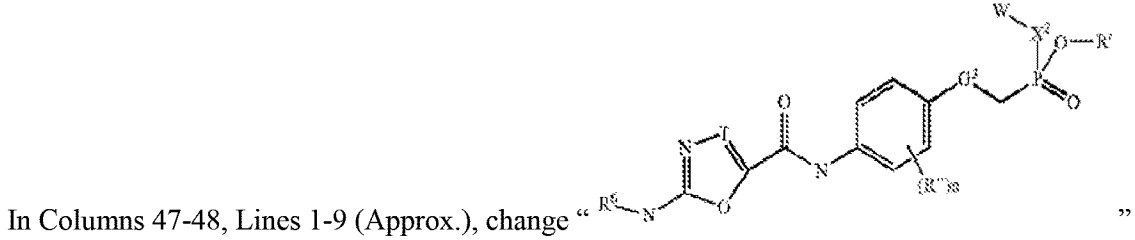 "

CERTIFICATE OF CORRECTION (continued)
U.S. Pat. No. 10,034,891 B2 to -- 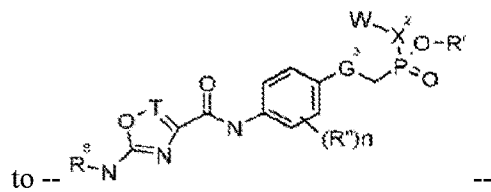 --

In Column 51, Line 59, change "didecanloyl" to -- dodecanoyl--

In Column 55, Line 26 (Approx.), change "2845-2885." to --284S-288S.--

In the Claims

In Column 56, Line 21, Claim 1, change "—OR$^a$" to -- —OR$^a$,--

In Column 56, Line 23, Claim 1, change "—NR$^a$CO NR$^a$R$^b$," to -- —NR$^a$CONR$^a$R$^b$,--

In Column 56, Line 23, Claim 1, change "—S(O)$_2$ NR$^a$R$^b$" to -- —S(O)$_2$NR$^a$R$^b$--

In Column 56, Line 32, Claim 1, change "—N(R$^a$ R$^b$)," to -- —N(R$^a$R$^b$),--

In Column 56, Line 44, Claim 1, change "(C$_1$- C$_4$)alkyl;" to --(C$_1$-C$_4$)alkyl;--

In Column 58, Line 6, Claim 1, change "—(CR$^a$R$^b$)$_t$N(R$^a$ R$^b$)" to -- —(CR$^a$R$^b$)$_t$N(R$^a$R$^b$)--

In Column 58, Line 18 (Approx.), Claim 1, change "6-or" to --6- or--